US006702805B1

(12) United States Patent
Stuart

(10) Patent No.: US 6,702,805 B1
(45) Date of Patent: Mar. 9, 2004

(54) MANIPULATOR

(75) Inventor: J. Michael Stuart, Corrales, NM (US)

(73) Assignee: Microdexterity Systems, Inc., Memphis, TN (US)

( * ) Notice: Subject to any disclaimer, the term of this patent is extended or adjusted under 35 U.S.C. 154(b) by 359 days.

(21) Appl. No.: 09/710,631

(22) Filed: Nov. 9, 2000

Related U.S. Application Data
(60) Provisional application No. 60/165,046, filed on Nov. 12, 1999.

(51) Int. Cl.[7] ............................................. A61B 17/00
(52) U.S. Cl. ........................... 606/1; 606/130; 600/102
(58) Field of Search .................... 606/1, 130; 600/102; 901/27, 15, 16; 248/276.1, 278.1, 281.11, 284.1

(56) References Cited

U.S. PATENT DOCUMENTS

| 3,923,166 A | 12/1975 | Fletcher et al. | |
|---|---|---|---|
| 3,949,747 A | 4/1976 | Hevesy | |
| 4,401,433 A | 8/1983 | Luther | |
| 4,527,446 A | * 7/1985 | Borodin | 901/21 |
| 4,573,452 A | 3/1986 | Greenburg | |

(List continued on next page.)

FOREIGN PATENT DOCUMENTS

EP  0009447  4/1980

OTHER PUBLICATIONS

Shai–Syg Motion & Innovations Ltd.; Robolite; copy of internet home page. Applicants first became aware of this material in Jun. 1998.

MicroE Inc.; copies of internet brochure pages of Rotary Micro Encoder and Linear Micro Encoder. Applicants first became aware of this material in Aug. 1998.

Computer Optical Products, Inc.; copies of internet home page and application notes relating to Hathaway Motion Control. Applicants first became aware of this material in Aug. 1998.

(List continued on next page.)

*Primary Examiner*—Linda C. M. Dvorak
*Assistant Examiner*—Jocelyn Ram

(57) ABSTRACT

A manipulator for producing a remote center of revolute motion is provided. The manipulator includes a base and a first parallelogram linkage mechanism including a first link pivotally mounted to the base for rotation about a first axis such that the first link moves in a first plane. The manipulator also includes a second parallelogram linkage mechanism including a second link pivotally mounted to the base for rotation about a second axis such that the second link moves in a second plane parallel to the first plane. The first link is pivotal about a third axis perpendicular to the first axis and the second link is pivotal about a fourth axis perpendicular to the second axis. The first and second parallelogram linkages are pivotally connected together by a first connector link and a second connector link. The first and second connector links are parallel to each other and parallel to the first and second axes such that the first and second planes remain parallel as the first and second links respectively rotate about the third and fourth axes. A tool holder is pivotally connected to the first connector link by a first pivot joint and pivotally connected to the second connector link by a second pivot joint such that a tool held therein is pivotable at a remote virtual pivot point about a first remote pivot axis by pivoting the first and second links respectively about the first and second axes and a second remote pivot axis by pivoting the first and second links respectively about the third and fourth axes.

38 Claims, 24 Drawing Sheets

U.S. PATENT DOCUMENTS

| | | | |
|---|---|---|---|
| 4,653,509 A | | 3/1987 | Oloff et al. |
| 5,053,687 A | | 10/1991 | Merlet |
| 5,078,140 A | | 1/1992 | Kwoh |
| 5,081,381 A | | 1/1992 | Narasaki |
| 5,086,401 A | | 2/1992 | Glassman et al. |
| 5,142,930 A | | 9/1992 | Allen et al. |
| 5,161,542 A | | 11/1992 | Palestrant |
| 5,186,174 A | | 2/1993 | Schlondorff et al. |
| 5,234,000 A | | 8/1993 | Hakky et al. |
| 5,240,011 A | | 8/1993 | Assa |
| 5,251,127 A | | 10/1993 | Raab |
| 5,279,309 A | | 1/1994 | Taylor et al. |
| 5,280,427 A | | 1/1994 | Magnusson et al. |
| 5,299,288 A | | 3/1994 | Glassman et al. |
| 5,305,203 A | | 4/1994 | Raab |
| 5,343,385 A | * | 8/1994 | Joskowicz et al. ............ 700/57 |
| 5,354,158 A | | 10/1994 | Sheldon et al. |
| 5,383,454 A | | 1/1995 | Bucholz |
| 5,389,101 A | | 2/1995 | Heilbrun et al. |
| 5,397,323 A | * | 3/1995 | Taylor et al. ............... 606/130 |
| 5,402,801 A | | 4/1995 | Taylor |
| 5,408,409 A | | 4/1995 | Glassman et al. |
| 5,415,182 A | | 5/1995 | Chin et al. |
| 5,417,210 A | | 5/1995 | Funda et al. |
| 5,425,616 A | | 6/1995 | Arai et al. |
| 5,445,166 A | | 8/1995 | Taylor |
| 5,464,013 A | | 11/1995 | Lemelson |
| 5,494,034 A | | 2/1996 | Schlondorff et al. |
| 5,564,436 A | | 10/1996 | Hakky et al. |
| 5,568,593 A | | 10/1996 | Demarest et al. |
| 5,571,072 A | * | 11/1996 | Kronner ..................... 600/102 |
| 5,572,999 A | | 11/1996 | Funda et al. |
| 5,584,292 A | | 12/1996 | Cheung |
| 5,628,327 A | | 5/1997 | Unger et al. |
| 5,630,431 A | | 5/1997 | Taylor |
| 5,643,286 A | | 7/1997 | Warner et al. |
| 5,647,373 A | | 7/1997 | Patielti |
| 5,695,500 A | | 12/1997 | Taylor et al. |
| 5,748,767 A | | 5/1998 | Raab |
| 5,749,362 A | | 5/1998 | Funda et al. |
| 5,776,153 A | | 7/1998 | Rees |
| 5,782,764 A | | 7/1998 | Werne |
| 5,800,423 A | * | 9/1998 | Jensen ........................... 606/1 |
| 5,803,912 A | | 9/1998 | Siczek et al. |
| 5,806,518 A | | 9/1998 | Mittelstadt |
| 5,817,084 A | * | 10/1998 | Jensen ........................... 606/1 |
| 5,825,536 A | * | 10/1998 | Yasunaga et al. ...... 248/281.11 |
| 5,833,656 A | | 11/1998 | Smith et al. |
| 5,851,183 A | | 12/1998 | Bucholz |
| 5,865,744 A | | 2/1999 | Willmen |
| 5,887,121 A | | 3/1999 | Funda et al. |
| 5,943,914 A | | 8/1999 | Morimoto et al. |
| 5,950,629 A | | 9/1999 | Taylor et al. |
| 5,951,475 A | | 9/1999 | Gueziec et al. |
| 5,976,156 A | | 11/1999 | Taylor et al. |
| 6,000,297 A | | 12/1999 | Morimoto et al. |
| 6,021,342 A | | 2/2000 | Brabrand |
| 6,024,695 A | | 2/2000 | Taylor et al. |
| 6,231,565 B1 | * | 5/2001 | Tovey et al. ................... 606/1 |
| 6,368,332 B1 | * | 4/2002 | Salcudean et al. .......... 606/130 |
| 2001/0027313 A1 | * | 10/2001 | Shimmura et al. ............. 606/1 |

OTHER PUBLICATIONS

Renishaw; copies of internet home page and product page for Encoder System. Applicants first became aware of this material in Aug. 1998.

Del–Tron Precision Inc.; copies of internet brochure order form for Ball Slide Assemblies, Crossed Roller Slide Assemblies and Ball Slide Positioning Stages. Applicants first became aware of this material in Aug. 1998.

Encoder Products Company; copies of internet product guide for Model 770 C and Model 775. Applicants first became aware of this material in Aug. 1998.

Stoianovici et al., "A Modular Surgical Robotic System for Guided Percutaneous Procedures." Applicants first became aware of this article in Apr. 2000.

* cited by examiner

MANIPULATOR

CROSS-REFERENCE TO RELATED APPLICATION

This application claims the benefit of United States Provisional Application No. 60/165,046 filed Nov. 12, 1999, the disclosure of which is incorporated herein by reference.

FIELD OF THE INVENTION

This invention relates to a manipulator capable of manipulating a tool or other object with one or more rotational degrees of freedom in a spherical coordinate system.

BACKGROUND OF THE INVENTION

In various applications, it is desirable to be able to pivot a tool or other object about a point in space which is remote from equipment supporting the tool. Such a point in space is sometimes called a virtual pivot point or a remote center of motion. An example of a situation in which it is useful to be able to pivot a tool about a virtual pivot point is in medical procedures. A medical tool often needs to be pivoted about a point in, on, or in proximity to a patient's body, but it may be undesirable to have support structure for the tool located at the point, since the support structure may introduce contamination into the patient's body or interfere with the view of or access to the patient by persons performing the medical procedures. A manipulator which can pivot a tool about a virtual pivot point can avoid such disadvantages of support structure.

One known type of manipulator capable of pivoting a tool in proximity to a virtual pivot point employs a parallel linkage to maintain the orientation of a rod-like tool remotely from the actuation point. The parallel linkage is attached to a rotating base assembly or has some other similar rotating structure at the base which allows the tool to be manipulated in two degrees of freedom (DOF) in a spherical coordinate system. An example of such a manipulator is described in U.S. Pat. No. 5,397,323 entitled "Remote Center-Of-Motion Robot For Surgery". This and other conventional parallel linkage manipulators have the drawback that the virtual pivot point must lie on a rotational axis of two of the links of the linkage. More specifically, the virtual pivot point must lie in the same plane as the rotational axis of the base and must be inline with the distal pivots of the manipulator. The manipulator disclosed in U.S. Pat. No. 5,397,323 only produces an approximate remote center of motion if the tool is mounted in from the distal pivots, since the tool actually sweeps an arc in one plane rather than pivoting around a point.

One disadvantage of these constraints on the location of the virtual pivot point is that it can be difficult to position the manipulator with respect to a patient's body and other equipment. In particular, the requirement that the virtual pivot lie in the same plane as the rotating structure at the base can cause clearance problems with a patient or with other equipment being used in the medical procedure such as imaging equipment. The clearance problems can require the patient or a person performing a medical procedure to assume an uncomfortable position.

In addition, the requirement that the virtual pivot point be inline with the distal pivots of the manipulator can make conventional parallel linkage manipulators difficult to use in biopsies and other medical procedures performed in conjunction with imaging systems such as computer tomography (CT) equipment, x-ray equipment or magnetic resonance imaging equipment. In a biopsy performed using imaging equipment, a biopsy needle is inserted into a patient's body while the patient is outside the imaging equipment. The patient is then placed inside the imaging equipment and an image is taken to determine the location of the biopsy needle with respect to the region of the body where the biopsy is to be performed. It is frequently difficult or unsafe for a human operator to adjust the position of the biopsy needle while an image is being taken. For example, there often is a very limited amount of space between the interior of the imaging equipment and the patient's body. Additionally, the operator could be exposed to harmful radiation from the imaging equipment or the operator could interfere with the imaging process. Thus, each time the position of the biopsy needle has to adjusted, the patient is withdrawn from the imaging equipment and then reintroduced into the imaging equipment after the position of the biopsy needle has been adjusted. Obviously, such a procedure is very time consuming and imprecise.

Recent advances in CT technology have decreased the time to generate an image to the point that near real time video images can be produced. With this technology, a doctor can place a medical tool with high precision, but he must be very close to the radiation source and receives a higher dose of harmful radiation.

One way in which these problems can be addressed is by using a manipulator that is capable of adjusting the position of a needle or object with respect to a patient's body while imaging is being carried out. However, with conventional parallel linkage manipulators that can produce a remote center of motion, the distal pivots are in the same plane as the image of interest and tend to distort that image. If the tool is offset from the distal pivots of the manipulator, as is the case with the manipulator described in U.S. Pat. No. 5,397,323, the tool will no longer rotate about a true virtual pivot point. Instead, the tool will move in a small arc as the manipulator is swung about.

SUMMARY OF THE INVENTION

Accordingly, in view of the foregoing, a general object of the present invention is to provide a manipulator capable of manipulating a tool or other object with two rotational degrees of freedom about a virtual pivot point with fewer constraints on the position of the manipulator relative to the virtual pivot point than with conventional manipulators.

Definition Of Terms

The term link will be used herein to refer to a member which functions as the equivalent of a rigid body when moving parallel to a specific plane. Thus, a link may be a rigid body, or it may comprise a plurality of components which can move together as a single body parallel to the specific plane but which are movable with respect to each other in a plane transverse to the specific plane. For example, in some embodiments, a group of components which function as a parallel linkage for movement parallel to a first plane may function as a single link for movement parallel to a second plane transverse to the first plane.

Two links are considered parallel to each other when a line connecting two rotational axes of one link is parallel to a line connecting two rotational axes of the other link.

The term pivot point will be used to refer to a point at which a link is physically connected to another member for pivoting with respect to the other member about an axis, while the term virtual pivot point will refer to a point in space at which a link can pivot about an axis passing through the virtual pivot point without the link having to be physically supported at the virtual pivot point. Pivot can provide one, two or three degrees of rotational freedom.

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF PREFERRED EMBODIMENTS

Figure 1:
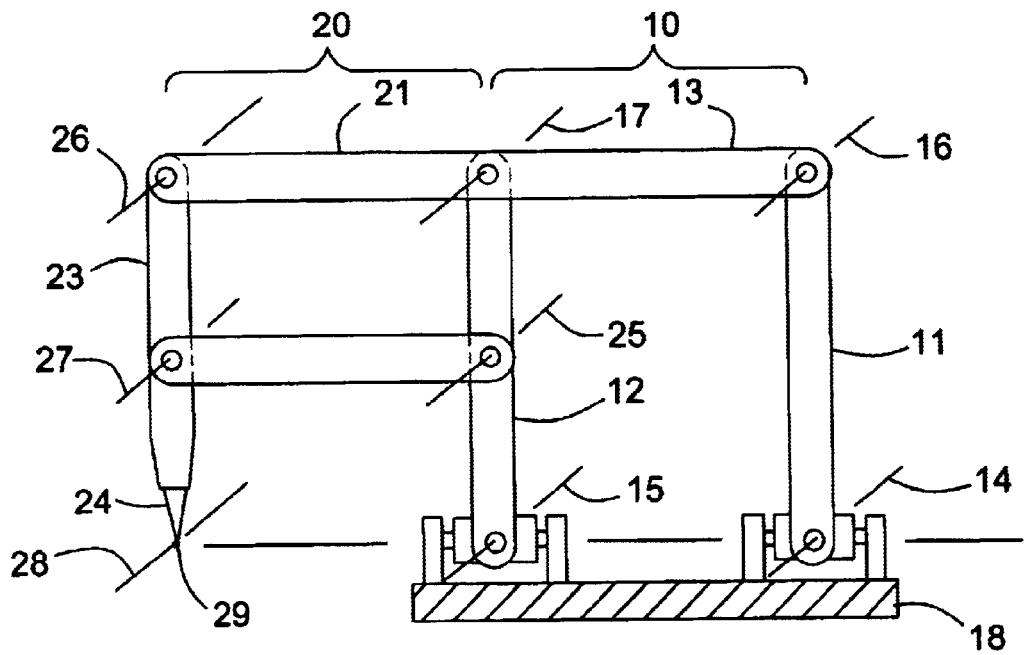
FIG. 1 is a schematic side elevation of a kinematic model of an example of a conventional parallel linkage manipulator.

Referring now more particularly to FIG. 1 of the drawings there is schematically shown a kinematic model of a conventional parallel linkage manipulator in which the virtual pivot point or remote center of motion produced by the manipulator is constrained to lie in the same plane as the roll axis of the main mechanism and to be inline with the distal pivots. The illustrated conventional manipulator includes two parallel linkages 10 and 20, each linkage having a plurality of links movable parallel to the plane of the drawing. For ease of viewing, the rotational axes of the links are shown extending diagonally, but they actually extend perpendicular to the plane of the drawing.

A first parallel linkage 10 includes three links 11, 12, and 13. Links 11 and 12 are pivotable about parallel axes 14 and 15 at their lower ends, which may be supported by a base 18 or other support structure such that axes 14 and 15 remain stationary with respect to each other. Links 11 and 12 are also pivotably connected to link 13 at their upper ends for pivoting about axes 16 and 17, which are both parallel to axis 14. A plane containing axes 16 and 17 is parallel to a plane containing axes 14 and 15, and a plane containing axes 14 and 16 is parallel to a plane containing axes 15 and 17.

The second parallel linkage 20 includes four links, i.e., link 12, link 21, link 22, and link 23 which supports a tool 24. Link 21, which is rigidly connected to link 13, is pivotably connected at its opposite ends to links 12 and 23 for pivoting about axis 17 and axis 26, which are parallel to axis 14. Link 22, in turn, is pivotably connected at its opposite ends to links 12 and 23 for pivoting about axis 25 and axis 27, both of which are parallel to axis 14. Axis 26 is coplanar with axes 16 and 17. A plane containing axes 25 and 27 is parallel to a plane containing axes 17 and 26. Axis 25 is coplanar with axes 15 and 17 and lies in a plane parallel to a plane containing axes 26 and 27.

When links 11 and 12 are simultaneously pivoted about axes 14 and 15, link 23 and the tool 24 pivot about axis 28 at a virtual pivot point 29. Because axis 26 is coplanar with axes 16 and 17, the virtual pivot point 29 is constrained to lie in a plane containing axes 14 and 15. Moreover, the virtual pivot point 29 is also constrained to be inline with the pivots connecting link 23 to links 21 and 22. As described above, depending on the situation and application, these constraints can create problems. In particular, in medical applications, the fact that the virtual pivot point 29 is constrained to lie in a plane containing axes 14 and 15 can make it difficult to provide adequate clearance between the manipulator and portions of the patient's body not involved in the procedure and between the manipulator and any other equipment involved in the procedure such as imaging equipment. The constraint that the virtual pivot point 29 be inline with the pivotal attachments of link 23 raises difficulties when the manipulator is used in conjunction with imaging equipment. In particular, link 23, which supports the tool, is typically in the same plane as the image of interest and tends to distort that image.

Figure 2:
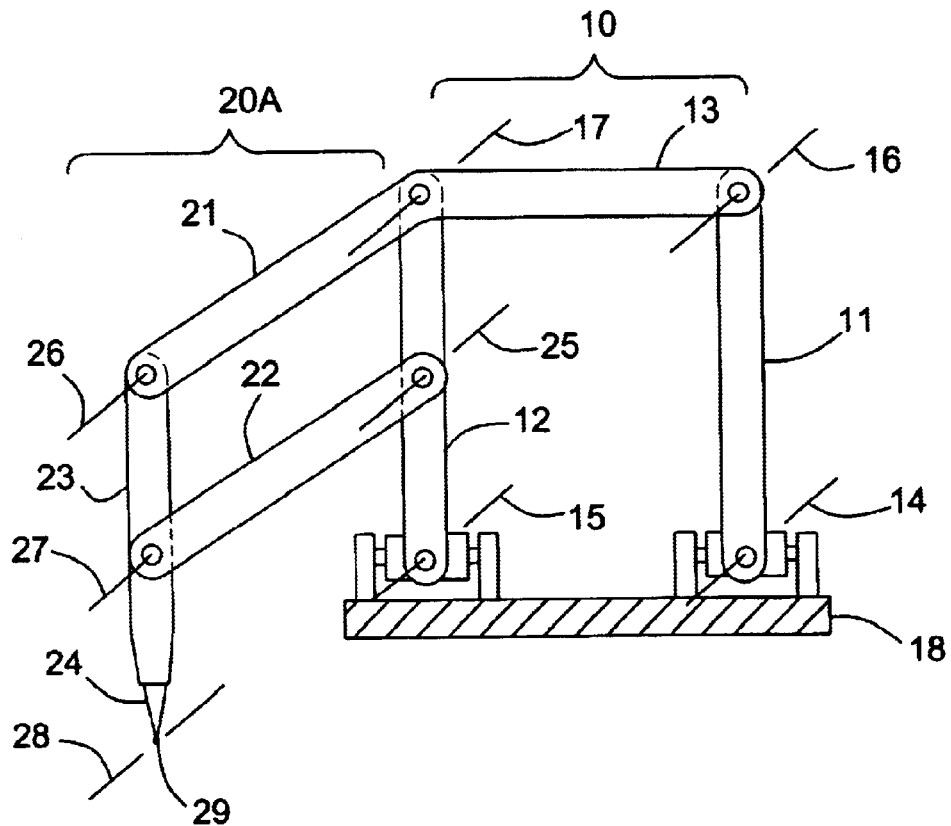
FIG. 2 is a schematic side elevation of a kinematic model of one aspect of a manipulator according to the present invention.

In accordance with one aspect of the present invention, a manipulator can be provided which does not have the virtual pivot point constraints that are associated with the conventional arrangement of FIG. 1. For example, FIG. 2 schematically illustrates a kinematic model of a manipulator according to the present invention in which the virtual pivot point is not constrained to be in the same plane as the base pivot axes 14 and 15. This manipulator is similar to that of FIG. 1 in that it includes two parallel linkages 10 and 20A, but link 21 of linkage 20A has been rotated with respect to link 13 relative to its orientation in FIG. 1 so that the two links 13 and 21 are no longer aligned, i.e., so that axis 26 is not coplanar with axes 16 and 17. Link 22 remains parallel to link 21.

As in FIG. 1, when links 11 and 12 are pivoted about axes 14 and 15, link 23 and the tool 24 which it supports pivot about axis 28 at virtual pivot point 29. However, since axis 26 is not coplanar with axes 16 and 17, axis 28 and thus the virtual pivot point 29 are spaced from the plane containing axes 14 and 15. This can make the manipulator of FIG. 2 more convenient to use than the manipulator of FIG. 1 and more comfortable for both an operator of the manipulator and a patient undergoing treatment. Depending upon whether link 21 is bent upward or downward with respect to link 13, the virtual pivot point 29 may be above or below the plane containing axes 14 and 15. The distance of the virtual pivot point 29 above or below the plane can be varied by varying the angle between links 13 and 21 or the lengths of the various links.

Figure 3:
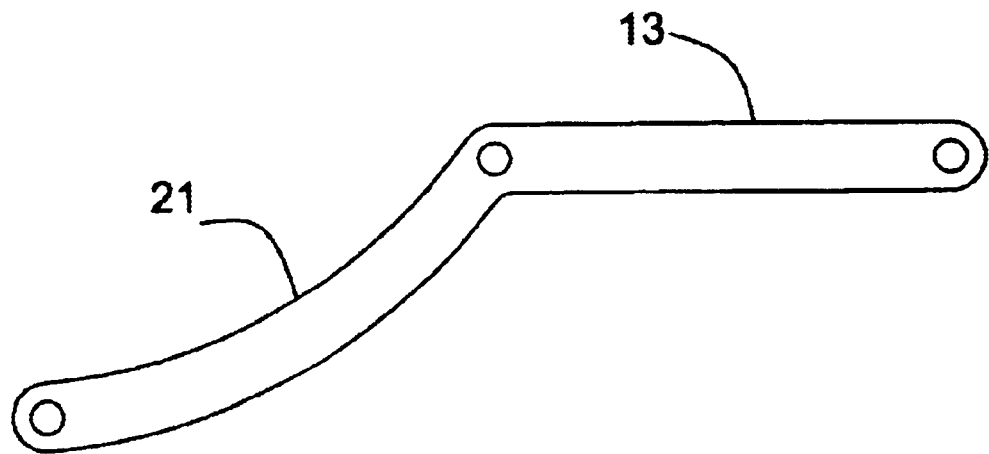
FIGS. 3 and 4 are schematic side views of two examples of links which can be employed in the present invention.
Figure 4:
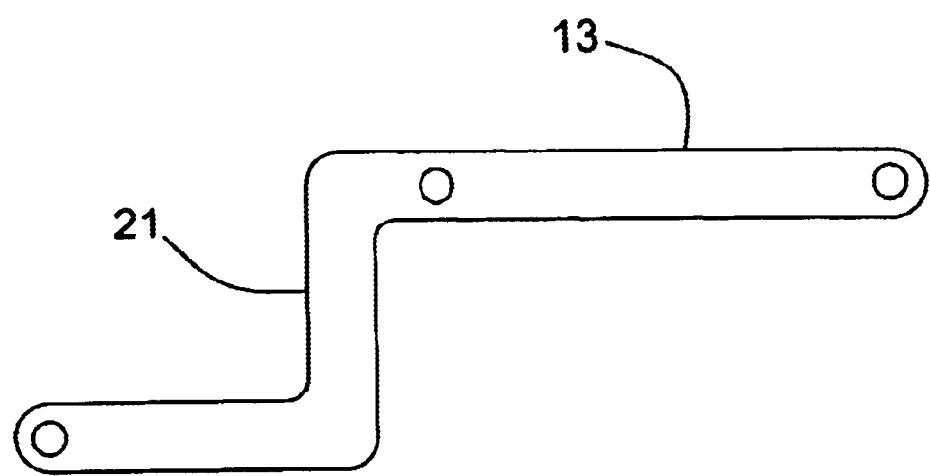
Figure 5:
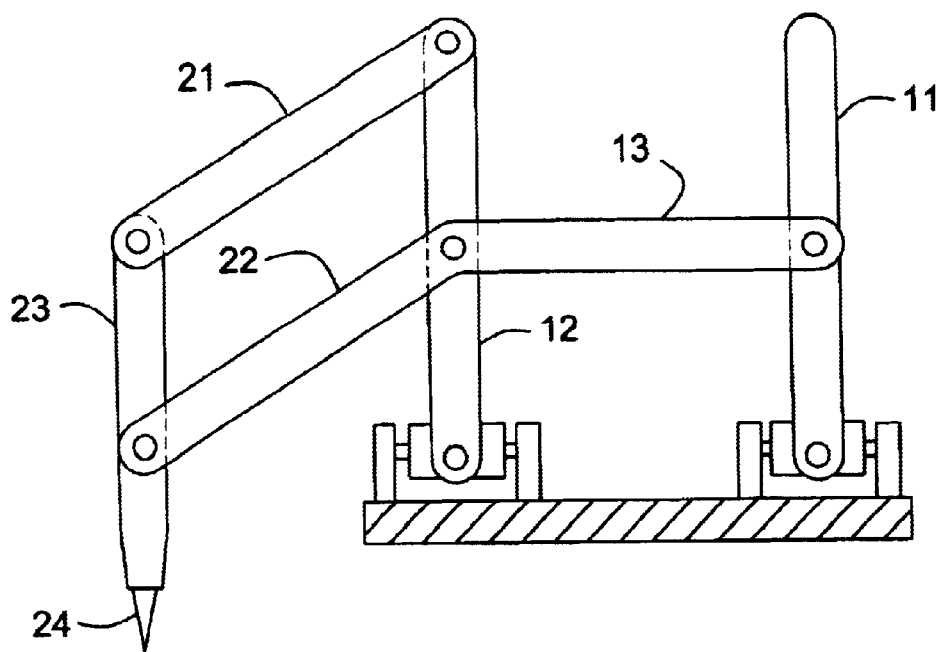
FIG. 5 is a schematic side elevation of a kinematic model of a variation of the example of FIG. 2.

In FIG. 2, links 13 and 21 are both straight members at an obtuse angle to each other, but they may have any shapes such that axis 26 is spaced from the plane containing axes 16 and 17. For example, link 21 can be curved or crank shaped, as schematically shown in FIGS. 3 and 4, respectively. Moreover, link 13 is shown rigidly connected to link 21 in FIG. 2, but, alternatively, it may be rigidly connected to link 22, as schematically shown in FIG. 5. Alternatively, link 13 may remain rigidly connected to link 21, and an additional link rigidly connected to link 22 may be pivotably connected between link 11 and link 12 parallel to link 13. Likewise, link 21 is illustrated as being integrally formed with link 13, but the two links may be separately formed and rigidly connected to each other in any suitable manner.

In FIG. 2, link 23 has a length such that the tip of the tool 24 coincides with the virtual pivot point 29, but the virtual pivot point 29 may be at any desired location with respect to link 23 and the tool 24. If the virtual pivot point 29 represents a point on the skin of a patient which is to be contacted by the tool 24, the lower end of the tool 24 may coincide with the virtual pivot point 29. If the tool 24 is to be inserted through an incision or other opening in the body of a patient to access a location within the patient's body, the virtual pivot point 29 may be a point within the body wall of the patient about which link 23 is to be pivoted, in which case the virtual pivot point 29 may coincide with a location on link 23 located above the tool 24. If the tool 24 is a laser or other device which is being used to treat a location on the patient's skin without contacting the location, the virtual pivot point 29 may coincide with the location on the skin and be spaced from both link 23 and the tool 24. Thus, the location of the virtual pivot point 29 with respect to link 23 and the tool 24 may vary depending upon the nature of the tool 24 and the type of procedure which is to be performed with the tool 24.

As will be appreciated, a manipulator according to the present invention can be used to manipulate a wide variety of objects, but it is particularly suitable for use in manipulating medical tools. A few examples of tools which can be used with a manipulator according to the present invention are cutting devices, needle holders, staples, forceps, clamps, probes, imaging devices, lasers, needles or other biopsy devices, devices for administering medication or other substances, or other devices for surgical, therapeutic, or diagnostic purposes. Moreover, while the present invention is described herein in connection with performing medical procedures, it will be readily appreciated that it is equally applicable to other types of applications involving manipulators.

Figure 6:
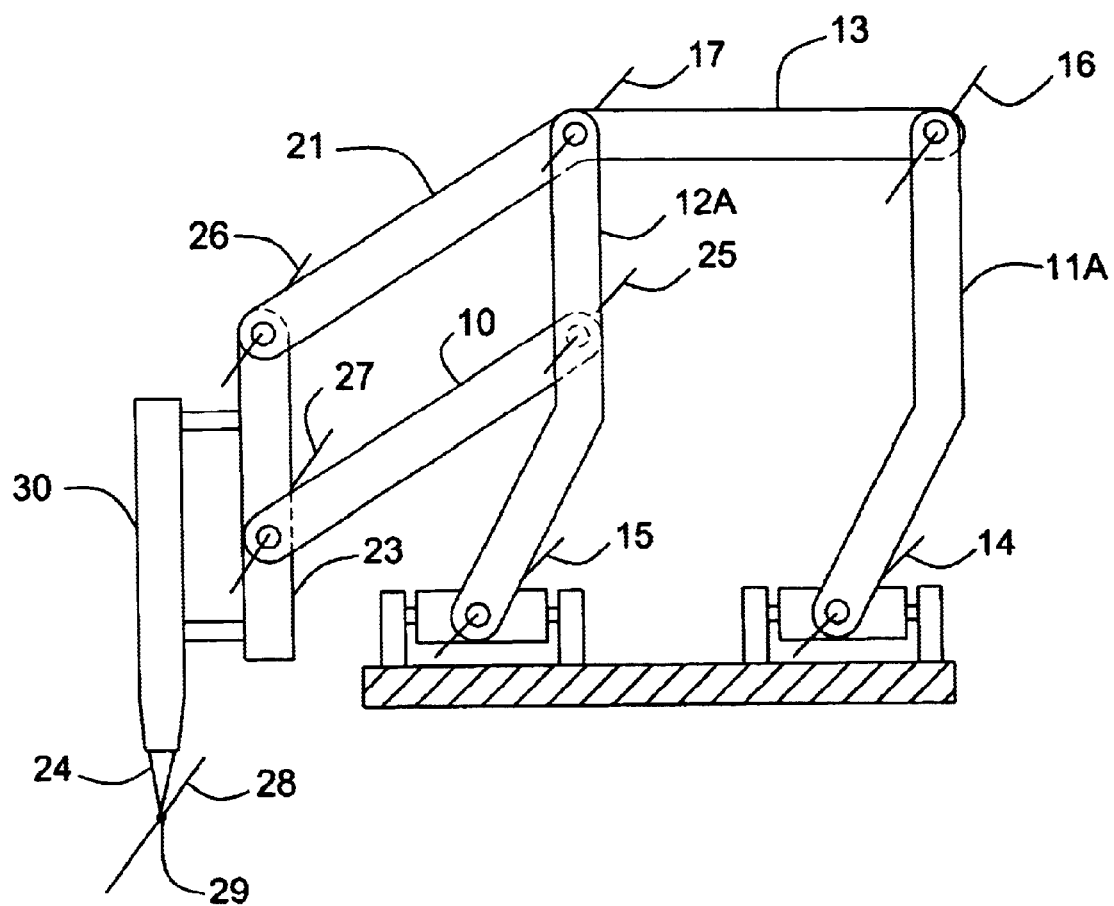
FIG. 6 is a schematic side elevation of a kinematic model of another variation of the example of FIG. 2.

In the embodiment shown in FIG. 2, the virtual pivot point 29 is still inline with the pivotal connections of the link 23 to links 21 and 22. Therefore, in order for the tool 24 to contact the virtual pivot point 29, the tool 24 must be mounted on link 23 inline with those pivotal connections. As noted above, this constraint can pose problems when the manipulator is used in conjunction with an imaging device in that link 23 obscures the image of the relevant area. Thus, according to another aspect of the present invention a manipulator can be provided in which the virtual pivot point is offset from the line defined by the pivots of link 23. As schematically shown in FIG. 6, by appropriately shaping the links of a manipulator, the virtual pivot point 29 can be spaced from the line defined by the pivots of link 23 supporting the tool 24. The manipulator of FIG. 6 is generally similar to the manipulator of FIG. 2, but link 12 of FIG. 2, for which axes 25, 17, and 15 are coplanar, has been replaced by a link 12A having a shape such that axis 25 is spaced from a plane connecting axes 15 and 17. Link 11A, which is parallel to link 12A, is shown having a non-linear shape similar to that of link 12A, but it may have any shape such that a plane containing axes 14 and 16 is parallel to a plane containing axes 15 and 17. Except for links 11A and 12A, the arrangement of the links is the same as in FIG. 2. The manipulator illustrated in FIG. 6 would function identically if it is arranged similar to the link arrangement in FIG. 5 with only links 11A and 12A being substituted for links 11 and 12.

As in the previous examples, when links 11A and 12A are pivoted about axes 14 and 15, link 23 and the tool 24 which it supports pivot about an axis 28, which is parallel to axis 14, at a virtual pivot point 29. However, due to the shape of link 12A, the virtual pivot point 29 is spaced from a line defined by the pivots of link 23. Therefore, in this case, the tool 24 can be supported by a tool holder 30 which is spaced forward (with reference to FIG. 6) of link 23 and still contact the virtual pivot point 29. As will be appreciated, the virtual pivot point could be spaced rearward of link 23 by configuring link 12A such that axis 25 is spaced forward of the plane connecting axes 15 and 17 and configuring link 11A with a complementary shape. Moreover, varying the shape of links 11A and 12A can vary the distance that the virtual pivot point is offset from the pivots of link 23. The spatial relationship between axes 17, 25 and 15 is maintained in the spatial relationship between axes 26 and 27 and the axis 28 at the virtual pivot point. While the embodiment of the invention shown in FIG. 6 is also configured such that the links 13 and 21 are not in alignment so as to also offset the virtual pivot point 29 from the plane of pivots 14 and 15, the embodiment of the invention shown in FIG. 6 could also be configured such that links 13 and 21 are in alignment and the virtual pivot is in the plane of pivots 14 and 15.

Figure 7:
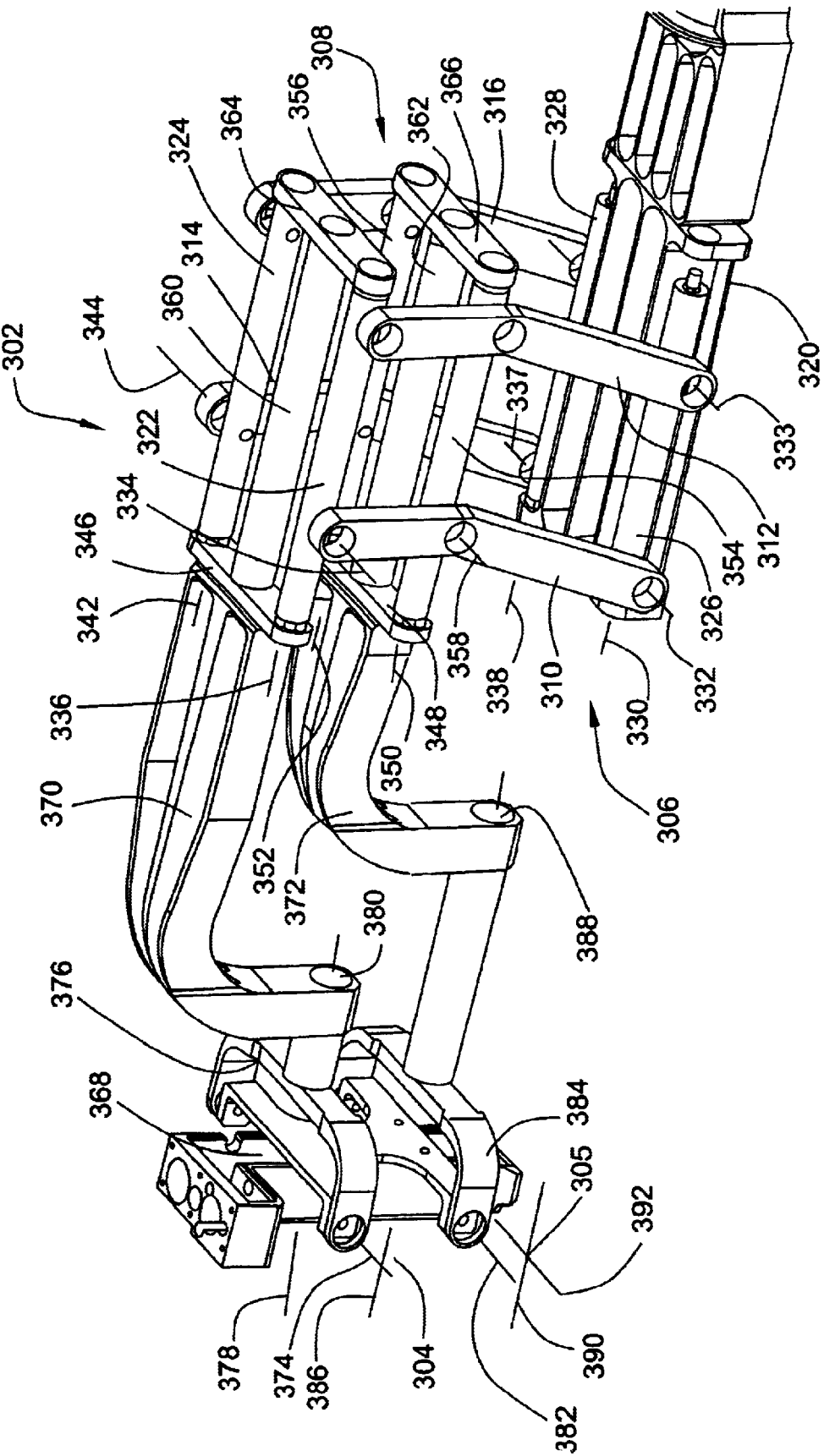
FIG. 7 is an isometric view of another embodiment of a manipulator constructed in accordance with the present invention.

In accordance with another aspect of the present invention, a manipulator can be provided which is capable of moving a tool about a virtual pivot point with two degrees of freedom. Specifically, in some instances, it may be sufficient to rotate a tool with a single degree of freedom about a single axis passing through a virtual pivot point. In other situations, it may be desirable to also rotate a tool with another degree of freedom about a second axis passing through the virtual pivot point, such as an axis perpendicular to the first axis. An illustrative embodiment of a manipulator 302 capable of producing movement of a tool 304 about a virtual pivot point 305 with two degrees of freedom is shown in FIG. 7. The manipulator 302 generally comprises two parallelogram linkage mechanisms 306, 308 that move in parallel planes and are linked together.

In the embodiment of the invention illustrated in FIG. 7, each of the two parallelogram linkage mechanisms 306, 308 comprises a 4-bar linkage. Each includes parallel front and rear vertical links 310, 312, 314, 316 that at one end are pivotally connected to a base 320 and a third horizontal link 322, 324 that pivotally connects the opposite ends of the front and rear vertical links. In each mechanism, the horizontal link 322, 324 is parallel to a line defined by the base pivots of the respective pair of vertical links 310, 312 and 314, 316. Each of the vertical links 310, 312, 314, 316 is mounted to the base 320 and to its respective horizontal link 322, 324 for pivotal movement about two perpendicular axes. In the illustrated embodiment this is accomplished by at the base pivots by pivotally connecting each vertical link to a corresponding roller 326, 328. For example, vertical link 310 is pivotally connected to a roller 326 which is rotatably supported by base 320. The pivotal connection to the roller 326 allows vertical link 310 to rotate about axis 332 while the roller allows vertical link 310 to rotate about axis 330. At the opposing end, vertical link 310 is pivotally connected to horizontal link 322 for rotation about axis 334. Horizontal link 322 is, in turn, rotatably supported such that vertical link 310 can rotate about axis 336 which is perpendicular to axis 334. The other vertical links 312, 314, 316 have similar pivotal connections to the base 320 and their respective horizontal link 322, 324 such that each is rotatable with two degrees of freedom with respect to the base and the corresponding horizontal link about two perpendicular axes. For ease of reference, besides the rotational axes for vertical link 310, only the rotational axes 337 and 338 for the connection of vertical link 314 to the base and the rotational axes 342 and 344 for the connection of vertical link 314 to horizontal link 324 are shown in FIG. 7.

As vertical links 310 and 314 are rotated respectively about axes 332 and 337 through operation of their respective parallelogram linkages, the vertical links 310 and 314 move in parallel planes. To ensure that these planes are constrained to move in parallel relation as the vertical links 310 and 314 rotate respectively about axis 330 and 338, the two parallelogram linkages 306, 308 are connected together at their forward ends by upper and lower connector links 346 and 348. The upper and lower connector links 346, 348 extend parallel to each other and interconnect, in this case, vertical link 310 of the first parallelogram linkage 306 and vertical link 314 of the second parallelogram linkage 308. In particular, the upper connector link 346 is pivotally connected adjacent one end to horizontal link 322 (and thereby vertical link 310) for rotation relative to vertical link 310 about axis 336 and adjacent the opposing end to horizontal link 324 (and thereby vertical link 314) for rotation relative to vertical link 314 about axis 342. Similarly, the lower connector link 348 is pivotally connected adjacent one end to vertical link 310 through an intermediate horizontal link 354 for rotation about axis 350 and adjacent the opposing end to vertical link 314 through an intermediate horizontal link 356 for rotation about axis 352.

To impart some stress into the manipulator 302 and thereby reduce the free play, the manipulator illustrated in FIG. 7 includes additional links and connections. In particular, each of the parallelogram linkage mechanisms 306, 308 includes an intermediate horizontal link 354, 356 which interconnects the two vertical links. Using the interconnection between vertical link 310 and intermediate horizontal link 354 as an example, vertical link 310 is pivotal about axes 350 and 358 relative to the intermediate horizontal link. In this instance, the pivotal movement about axis 350 is achieved via rotatably supporting the intermediate horizontal link 354 at either end in a similar manner to the horizontal links 322 and 324. As shown in FIG. 7, axis 350 is parallel to axis 336 and axis 358 is parallel to axis 334. The other vertical links have similar pivotal connections with the respective intermediate horizontal links. The illustrated manipulator further includes an upper support bar 360 extending parallel to the horizontal links 322, 324 of the two parallelogram linkages 306, 308 and an intermediate support bar 362 that extends parallel to the intermediate horizontal links 354, 356. Additionally, the manipulator includes rear connector links 364, 366 which interconnect vertical links 312 and 316 and horizontal links 322, 324 at the rear ends of the parallelogram linkages. The rear connector links 364, 366 and the upper and lower connector links 346, 348 at the forward end of the parallelogram linkages further serve the function of rotatably supporting the horizontal links 322, 324 and the intermediate horizontal links 354, 356.

Like the intermediate horizontal links 354, 356, the support bars 360, 362 and rear connector links 364, 366 are redundant and help introduce more rigidity into the manipulator 302 thereby reducing free play. This reduction in free play is useful in surgical applications, however, it will be appreciated that the intermediate horizontal links and support bars are not necessary parts of the present invention. Furthermore, while the illustrated embodiment produces certain pivotal movements by rotatably supporting either end of the horizontal links and the intermediate horizontal links, other types of pivotal connections between the various links could be used. Similarly, the upper and lower connector links could be connected directly to vertical links 310 and 314 rather than through the horizontal links 322, 324 and intermediate horizontal links 354, 356 as in the illustrated embodiment.

For supporting the tool 304 for rotary movement at the remote virtual pivot point 305 with two degrees of freedom, the manipulator 302 includes a tool holder link 368 that is pivotally connected to the upper connector link 346 and pivotally connected to the lower connector link 348. In the illustrated embodiment, the pivots for the tool holder link 368 are at the free end of extended portions of the connector links 370, 372 which extend parallel to each other and outwardly away from the forward end of the two parallelogram linkages. The pivotal connection of the tool holder link 368 with the upper connector link 346 permits pivotal movement about axis 374 (via yoke 376) and axis 378 (via pivot joint 380) which intersects and is perpendicular to axis 374. Similarly, the pivotal connection of the tool holder link 368 with the lower connector link 348 permits pivotal movement about axis 382 (via yoke 384) and axis 386 (via pivot joint 388) which intersects and is perpendicular to axis 382. With this arrangement, a tool held by the tool holder link 368 will rotate about axis 390 at the virtual pivot point 305 when the vertical links 310, 312 are pivoted side-to-side about axes 330 and 338 and the tool rotate about axis 392 at the virtual pivot point when the vertical links are pivoted front-to-back about axes 332 and 333. During this pivotal movement, the upper and lower connector links 346, 348 are constrained to move in parallel relation to each other by the two parallelogram linkage mechanisms 306, 308.

In the embodiment illustrated in FIG. 7, the vertical links 310, 312, 314, 316 are offset rearward such that the pivotal connection with the intermediate horizontal links 354, 356 (and in turn the lower connector link 348) is not co-linear with a line defined by the connections of the vertical links with the horizontal links 322, 324 and the base 320. This arrangement is similar to the one degree of freedom manipulator illustrated in FIG. 6 and results in a shift of the virtual pivot point forward from a line intersecting the pivotal connections of the tool support link.

Figure 9:
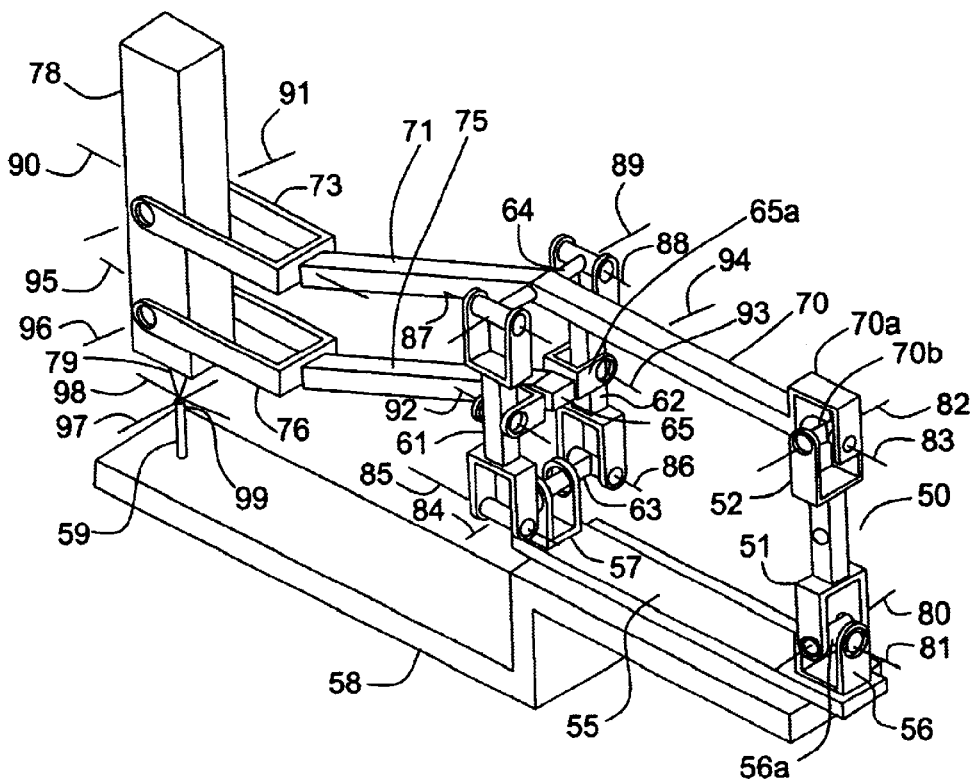
FIG. 9 is an isometric view of an embodiment of a manipulator according to the present invention.
Figure 10:
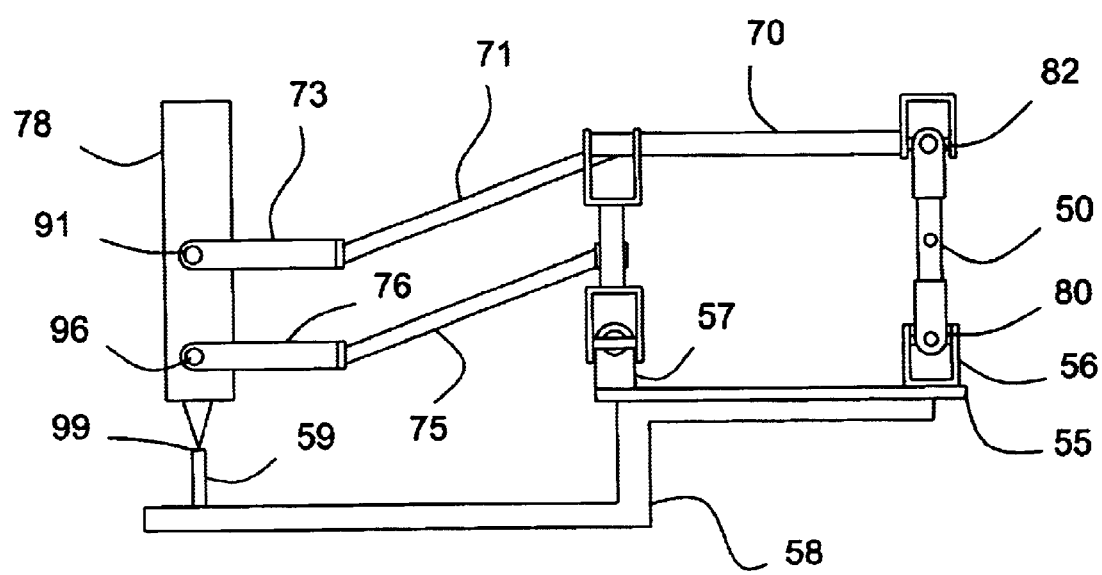
FIG. 10 is a side elevation of the embodiment of FIG. 9.

A further embodiment of a manipulator constructed in accordance with the present invention is illustrated in FIG. 9. The embodiment of FIG. 7 is over constrained and includes redundant links. In the embodiment of FIG. 9, these redundant links have been removed. The embodiment of FIG. 9 functions in the same manner as the FIG. 7 embodiment and can still be understood as being based on two parallelogram linkage mechanisms operating in parallel that are connected together. However, in the case of the embodiment of FIG. 9, the two parallelogram linkages share a common rear vertical link 50 and a common horizontal link 70. The intermediate horizontal links and the rear connector links of the FIG. 7 embodiment have been eliminated and there are no additional support bars in the manipulator.

Figure 8A:
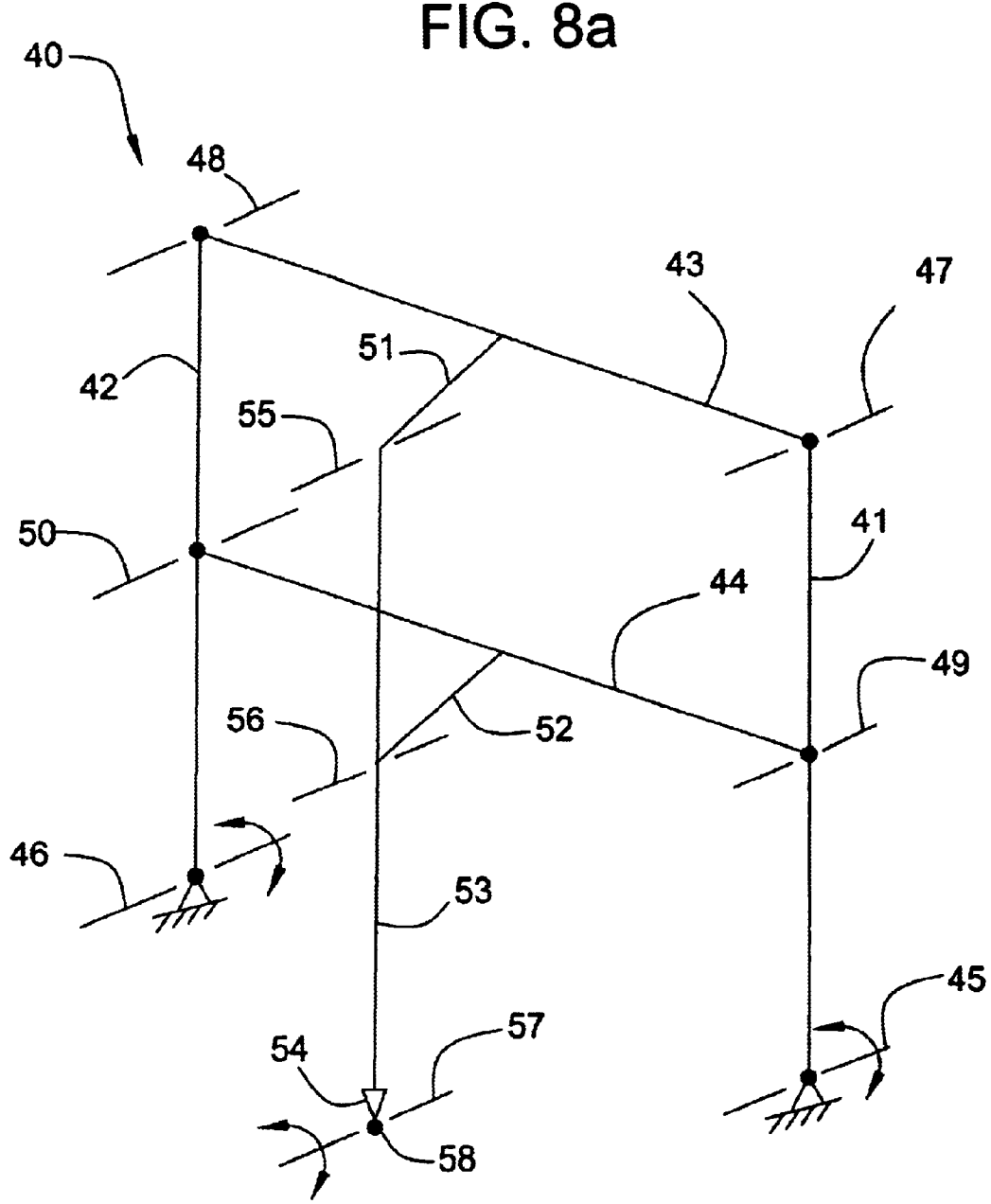
FIG. 8a is an isometric view and FIG. 8b is a front elevation of a kinematic model of another aspect of a manipulator according to the present invention.
Figure 8B:
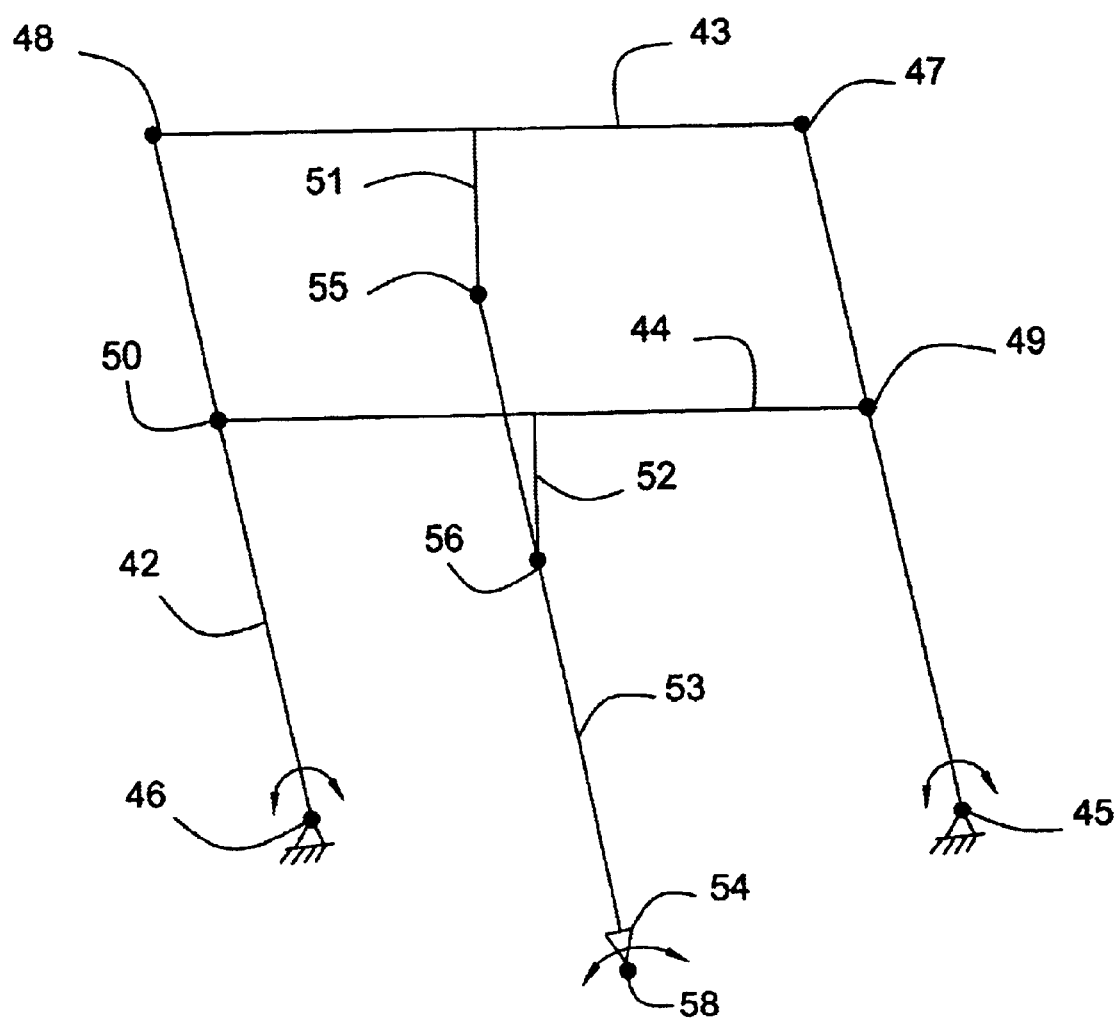

Another way in which the FIG. 9 embodiment can be understood is by taking a parallelogram linkage like that shown in FIG. 2 and replacing one of the parallel vertical links with a second parallelogram linkage which moves in a plane perpendicular to the first parallelogram linkage. To this end, FIG. 8a is a schematic isometric view of a manipulator, and FIG. 8b is a schematic front elevation of the manipulator pivoted sideways with respect to the vertical. The manipulator includes a parallel linkage 40 including links 41–44. Links 41 and 42, which are parallel to each other, are pivotable at their lower ends about parallel axes 45 and 46, respectively, with the lower ends of the links being supported by a base or other suitable structure such that axes 45 and 46 remain stationary with respect to each other. Links 43 and 44, which are parallel to each other, are each pivotably connected to links 41 and 42. Link 43 is pivotably connected to link 41 for pivoting about axis 47, and it is pivotably connected to link 42 for pivoting about axis 48. Link 44 is pivotably connected to link 41 for pivoting about axis 49 between axes 45 and 47, and it is pivotably connected to link 42 for pivoting about axis 50 between axes 46 and 48. All of axes 45–50 are parallel to each other.

Link 51 and link 52, which is parallel to link 51, extend transversely from link 43 and link 44, respectively. Links 51 and 52 remain in parallel relation as parallel linkage 40 moves from side to side in a plane and are illustrated as being rigidly connected to links 43 and 44, but they may be pivotably connected to links 43 and 44 if some means is provided for constraining links 51 and 52 such that they move in parallel relation to each other. Links 51 and 52 are pivotably connected to link 53, which supports a tool 54 at its lower end, for pivoting about axes 55 and 56, respectively, which are parallel to axis 45. Axis 55 is spaced from a plane containing axes 47 and 48, and axis 56 is spaced from a plane containing axes 49 and 50, while a plane containing axes 55 and 56 is parallel to a plane containing axes 45, 47, and 49.

With this arrangement, when links 41 and 42 are simultaneously pivoted about axes 45 and 46, as shown in FIG. 8b, link 53 and the tool 54 pivot at a virtual pivot point 58 about an axis 57 which is parallel to axis 45 but is spaced from a plane containing axes 45 and 46. Thus, by combining the aspect of the invention illustrated in FIGS. 7 and 8 with the aspect of the invention illustrated in FIG. 2, a manipulator according to the present invention can pivot a tool about a virtual pivot point with two degrees of freedom. For example, if link 12 of FIG. 2 is made a parallel linkage similar to linkage 40 of FIG. 8a, and if links 21 and 22 of FIG. 2 can pivot with respect to link 23 with two degrees of freedom, then a tool can be made to pivot with two degrees of freedom at a virtual pivot point about two orthogonal axes, such as axis 28 of FIG. 2 and axis 57 of FIG. 8a.

Referring again to the manipulator shown in FIGS. 9–15, the vertical link 50 is pivotably supported at its lower end by a base 55 for pivoting about axis 80 and axis 81 perpendicular to and intersecting axis 81. Two vertical links 61 and 62 extend parallel to each other and to vertical link 50. Vertical links 61 and 62 are supported by the base 55 for movement parallel to link 50. Like the FIG. 7 embodiment, vertical links 61 and 62 are interconnected by parallel upper and lower connector links 64 and 65. Horizontal link 70 is pivotably connected at one end to link 50 for pivoting about axis 82 parallel to axis 80 and about axis 83 perpendicular to and intersecting axis 83 and parallel to axis 81. At its other end, link 70 is pivotably connected to the upper connector link 64 for pivoting with respect to the upper connector link about axis 89 parallel to axis 82. The upper connector link is pivotally connected to vertical link 62 for pivotal movement about axes 88 and 89 and to vertical link 61 for pivotal movement about axes 87 and 89. The lower connector link 65 is pivotally connected to vertical link 62 for pivotal movement about axes 93 and 94 and to vertical link 61 for pivotal movement about axes 92 and 94.

As with the FIG. 7 embodiment, the upper and lower connector links 64 and 65 include respective extended portions 71 and 75 which extend parallel to each other for supporting a tool holder link 78. The tool holder link 78 is adapted to support a tool and is connected to the upper connector link extended portion 71 for pivotal movement about axis 90 parallel to axis 81 and about axis 91 (via yoke 73) perpendicular to and intersecting axis 90. The tool holder link 78 is connected to the lower connector link extended portion 75 for pivotal movement about axis 95 and about axis 96 (via yoke 76) perpendicular to and intersecting axis 95. The yokes 73 and 76 are pivotally connected to the ends of the extended portions of the upper and lower connector links 71 and 75 so as to produce the pivotal movement about axes 90 and 95.

The various links can be configured in a wide variety of ways and result in kinematically equivalent arrangements, all of which are included in the scope of the present invention. Thus, the structure shown in FIG. 9 is but one example of a manipulator according to the present invention. In the illustrated embodiment, vertical link 50 includes lower and upper yokes 51, 52 secured to opposite ends of the link. The lower yoke 51 is connected to a yoke 56 mounted on the base 55 by a spider 56a to define a universal joint pivotable about axes 80 and 81. The upper yoke 52 is connected to a yoke 70a on the end of link 70 by a spider 70b to define another universal joint pivotable about axes 82 and 83.

Vertical links 61 and 62 are similar in structure to link 50, each including a yoke at either end. The lower yoke of vertical link 61 is pivotably connected to a first end of a lower pivotal support 63 for pivoting about axis 85, and the upper yoke is pivotably connected to one end of the upper connector link 64 for pivoting about axis 87 which is parallel to axis 85. The lower yoke of link 62 is pivotably connected to the second end of the lower pivotal support 63 for pivoting about axis 86, which is parallel to axis 85, and the upper yoke of link 62 is pivotably connected to the second end of the upper connector link 64 for pivoting about axis 88, which is parallel to axis 85. The lower pivotal support 63 is pivotably supported by a yoke 57 mounted on the base 55 for pivoting about axis 84, which is parallel to axis 89. The lower connector link 65 includes two yokes 65a. One of the yokes 65a is pivotably connected to vertical link 61 and the other yoke 65a is pivotably connected to vertical link 62.

Figure 11:
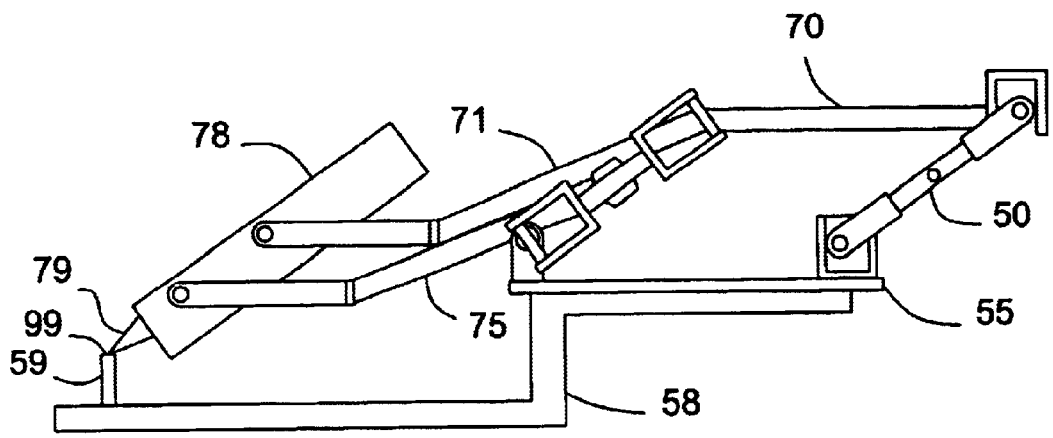
FIGS. 11 and 12 are respectively a side elevation and an isometric view of the embodiment of FIG. 9 rotated backwards from the position shown in FIG. 9.
Figure 12:
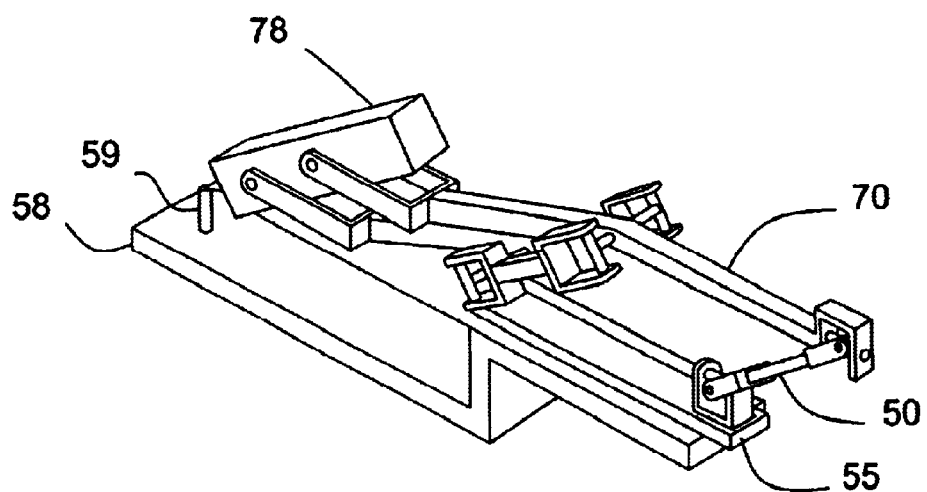
Figure 13:
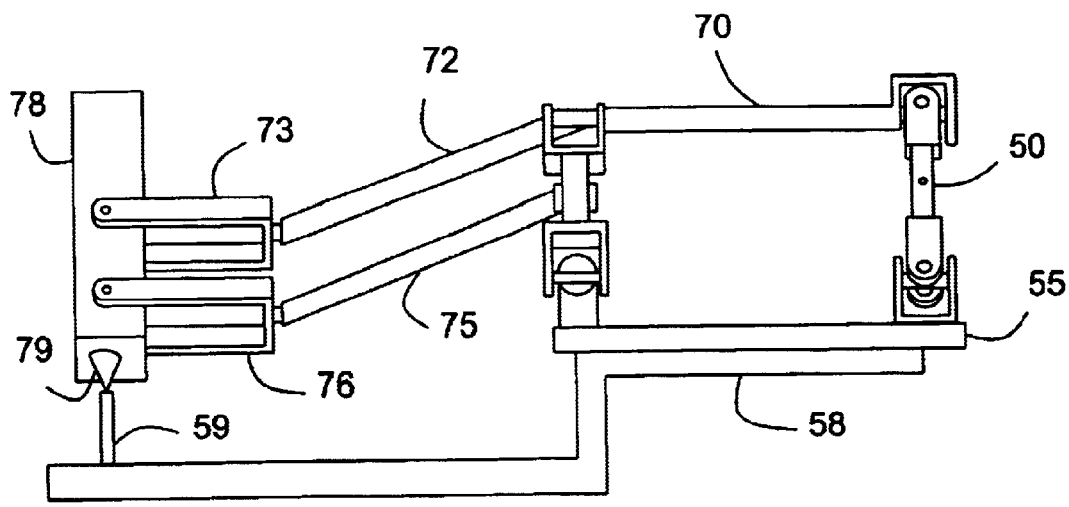
FIGS. 13, 14, and 15 are respectively a side elevation, an isometric view, and a front elevation of the embodiment of FIG. 9 rotated sideways from the position shown in FIG. 9.
Figure 14:
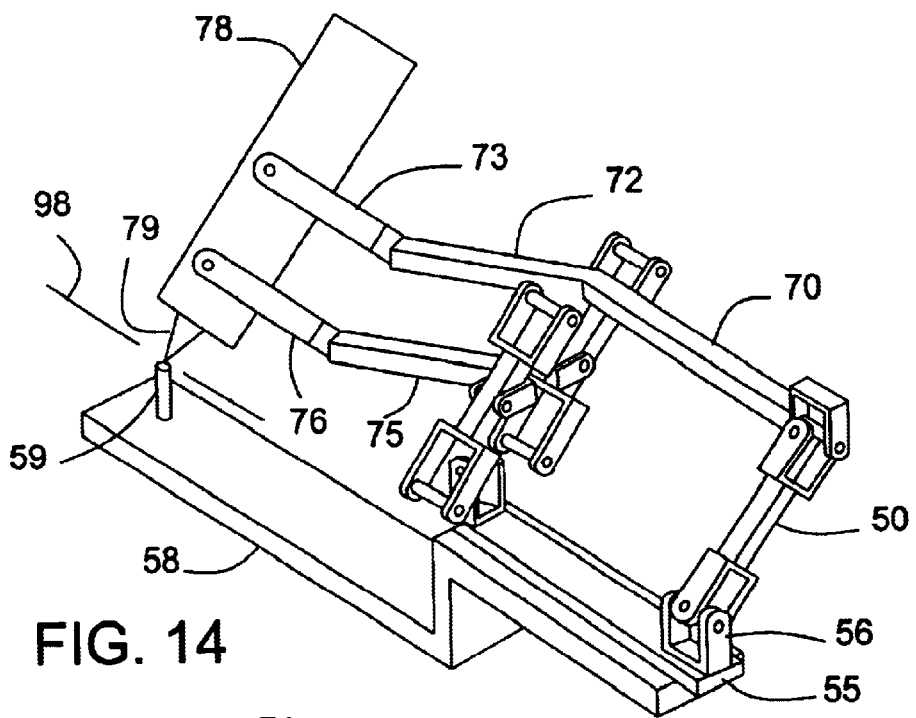
Figure 15:
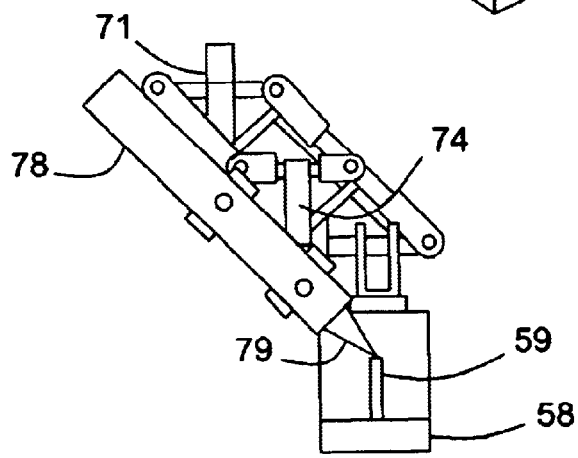

When vertical link 50 is pivoted about axis 80 and the vertical links 61 and 62 is pivoted about axis 84, as shown, for example, by FIG. 11, the manipulator behaves like the kinematic model of FIG. 2, with the interconnected vertical links 61 and 62 functioning as a single rigid link corresponding to link 12 of FIG. 2. As a result, the tool holder link 78 and the tool 79 pivot at a virtual pivot point 99 about axis 97, which is parallel to axis 84. When vertical link 50 is pivoted about axis 81 and vertical links 61 and 62 are pivoted about axes 85 and 86, respectively, as shown, for example, by FIGS. 14 and 15, the manipulator behaves like the kinematic model of FIGS. 8a and 8b, and link 78 and the tool 79 pivot at the virtual pivot point 99 about axis 98, which is parallel to axis 81 and perpendicular to axis 97 and intersects axis 97 at the virtual pivot point 99. The upper connector link extended portion 71, which corresponds to link 21 of FIG. 2, is not aligned with the horizontal link 70, so the virtual pivot point 99 is spaced from a plane containing axes 85 and 86.

The tool 79 may remain stationary with respect to the tool holder link 78, or the tool holder link 78 may include structure which enables the tool 79 to be manipulated with respect to the tool holder link 78 with one or more degrees of freedom. For example, the tool holder link 78 may be capable of translating the tool 79 in its axial direction, of rotating the tool 79 about its longitudinal axis, and of pitching and/or yawing the tool 79 with respect to the tool holder link 78.

Vertical links 50, 61, and 62 are shown pivotably supported by a common base 55, but they may be mounted on separate members. The base 55 is shown sitting on a crank-shaped support 58 having a support pin 59, the upper end of which represents the location of the virtual pivot point 99. However, the pin 59 performs no function in the operation of the manipulator and is present merely to make the location of the virtual pivot point 99 easier to identify in this figure. In actual use, the manipulator can be mounted on any convenient support member, which may be stationary or movable. For example, the manipulator may be mounted on a wall, a ceiling, a support stand, a movable gantry, an operating table, an imaging device or other medical device with which the manipulator is to be used, or the distal end of another manipulator.

In FIG. 9, the vertical links 61 and 62 are located between vertical link 50 and the tool holder link 78. Alternatively, the positions of vertical link 50 and the vertical links 61 and 62 can be interchanged, with vertical link 50 located between vertical links 61 and 62 and tool holder link 78.

The links of a manipulator according to the present invention can be of fixed length, or they can be of adjustable length to enable the location of the virtual pivot point to be adjusted without having to move the entire manipulator. An adjustable link can have a variety of structures. For example, it can be a member with telescoping or otherwise overlapping portions and which can be lengthened or shortened either by hand or by an actuator, such as a motor or a cylinder, connected between the different telescoping portions of the link.

Additionally, the extended portions 71, 75 of the upper and lower connector links are shown centered between the pivots of the vertical links 61 and 62. However, this is not necessary. The extended portions 71, 75 only need to be connected to the upper and lower connector links 64, 65 in a plane parallel to a plane containing link vertical link 50. By combining this possible linear translation of the attachment points of the extended portions 71, 75 with telescoping extended portions and angular variations between the extended portion 71 of the upper connector link and the horizontal link 70, three dimensional translational motion can be defined to allow the translation of the virtual pivot 99 to any point within the reach of the mechanism.

The manipulator of FIG. 9 can be operated by exerting a force on one or more of the vertical links 50, 61, and 62 to cause the link to pivot about its lower end. The manipulator can be operated manually or by actuators employing electrical, pneumatic, or hydraulic power, for example. When the manipulator is operated manually, one of the links, such as vertical link 50, can be directly grasped by the hand of a user, or a lever, a wheel, a crank, or other manually operable member can be mechanically coupled to one or more of the links to pivot the link with one or more degrees of freedom. Additionally, the manipulator configured such that it can be locked in position either by the actuators or by brakes or another type of mechanical lock.

Figure 16:
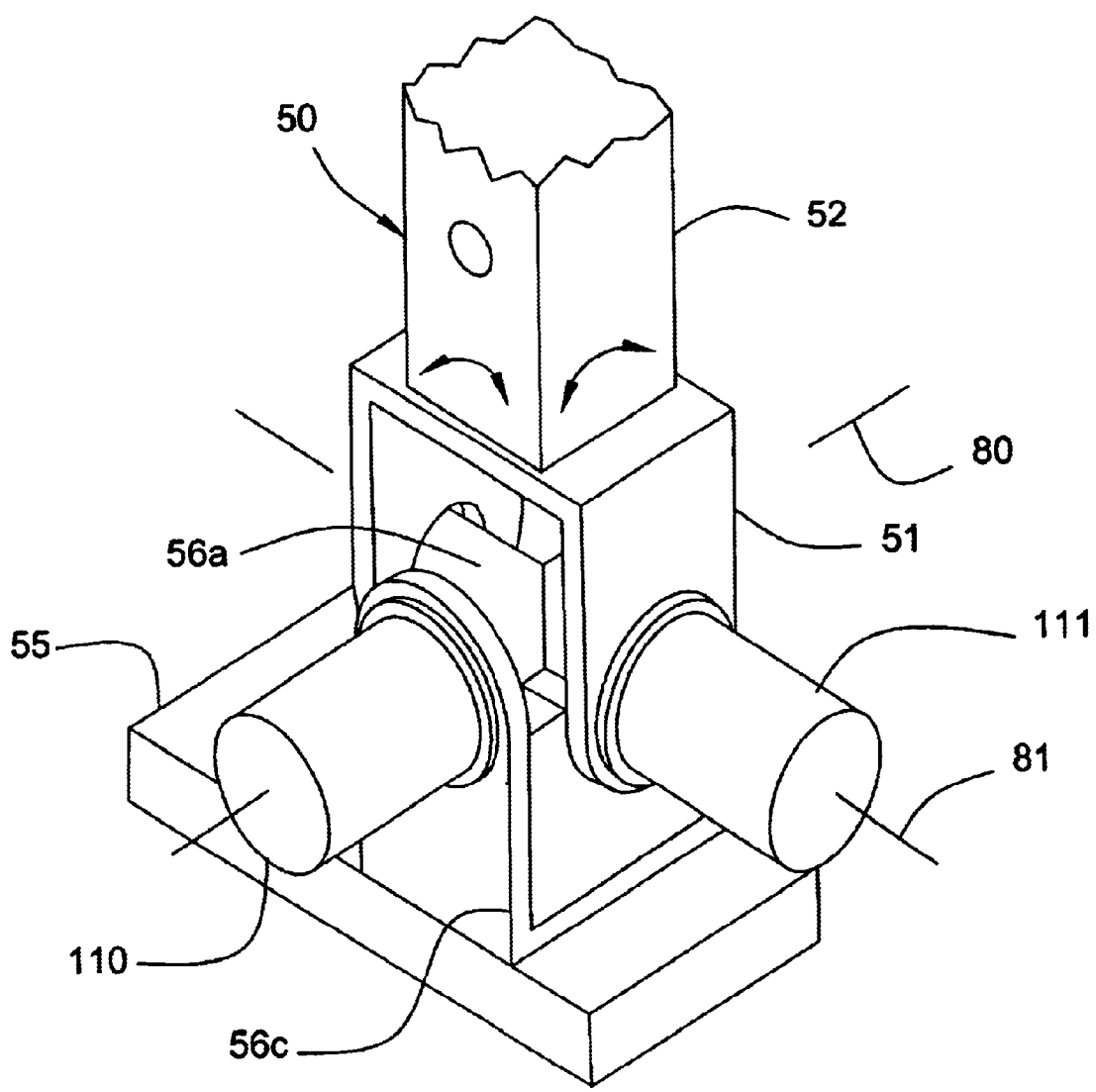
FIG. 16 illustrates an example of the use of motors to drive the embodiment of FIG. 9.

Actuators for driving the manipulator can be connected to the manipulator at a variety of locations to exert a torque on a link about one or more of the rotational axes. For example, as shown in FIG. 16, motors 110 and 111, which may include a reduction gear, can be mounted on each yoke 51, 56 of the universal joint at the lower end of vertical link 50. In this example, each motor 110, 111 has an output shaft coaxially secured to one leg of the spider 56a of the universal joint and a housing, with respect to which the output shaft can rotate, secured to the yoke so that when the motor is operated, the spider 56a and the yoke 51 or 56 are made to undergo relative rotation about the axis of the output shaft. When motor 110 is operated, vertical link 50 pivots about axis 80, and when motor 111 is operated, vertical link 50 pivots about axis 81. Alternatively, motors can be mounted on the lower yoke of one or both of vertical links 61 and 62 to pivot these links about axes 85 and 86, and a motor can be connected to lower pivotal support rod 63 to rotate the parallel linkage 60 about axis 84.

The motors may be controlled in response to signals from a suitable input device. In particular, the manipulator of the present invention can be used as a slave robot in a master-slave robotic system. In such a system, a surgeon/operator provides position input signals to the "slave" manipulator via a master or haptic interface which operates through a controller or control console. Specifically, through the use of an input device on the haptic interface such as a joystick, foot pedal or the like, the surgeon indicates the desired movement of the tool held by the manipulator. The haptic interface relays these signals to the controller which, in turn, applies various desired predetermined adjustments to the signals prior to relaying them to the slave manipulator. Any haptic interface can be used to control the manipulator via the controller. Other input devices such as a keyboard, a tape memory or other storage device, a mouse, a digitizer, a computer glove, or a voice operated controller could also be used.

Based on the signals provided by the controller, the manipulator executes the desired movement or operation of the tool. Thus, any desired dexterity enhancement can be achieved by setting up the controller to perform the appropriate adjustments to the signals sent from the haptic interface. For example, this can be accomplished by providing the controller with software which performs a desired dexterity enhancement algorithm. Software dexterity enhancement algorithms can include position scaling, force scaling, tremor filtering and gravity compensation. These and other examples of possible algorithms are well known in the field of robotics and described in detail in published literature.

The various actuators and/or the tool holder link can also be equipped with sensors for sensing the forces or torques applied thereon so as to enable a determination of the forces and torques applied to the tool. This information can again be used in a feedback control loop to the controller, for example to allow force feedback to the input device of the haptic interface. Of course, any known method for measuring forces and/or torques can be used, including, for example, foil type or semiconductor strain gauges or load cells. The forces also could be displayed on a display device for an operator of the manipulator. Additional details regarding input devices, controllers and actuators suitable for manipulators to be used in medical imaging environments is disclosed in commonly assigned U.S. application Ser. No. 09/442,966 entitled "Medical Manipulator For Use With An Imaging Device" which is hereby incorporated by reference.

In the manipulator embodiments shown in FIGS. 2–16, parallelogram mechanisms comprising four bar linkages are employed to constrain certain links to move in parallel relation as the manipulator swings back and forth to move a tool in space. However, as will be appreciated by those skilled in the art, parallelogram linkages other than four-bar linkages can perform a similar function. For example, another embodiment of a manipulator constructed in accordance with the present invention is shown in FIGS. 17–23. The embodiment of the invention shown in FIGS. 17–23 functions in the same manner as the embodiment shown for example in FIG. 7, however, instead of using two parallel four bar linkages that are linked together the embodiment of the invention shown in FIGS. 17–23 utilizes two parallel gear linkage mechanisms (referenced herein as first and second parallel gear linkage mechanisms).

Each of the gear linkage mechanisms includes a vertical link 150, 151. The vertical links 150, 151 are parallel to each other and, in this case, are identical. The lower end of the vertical link 150 of the first gear linkage mechanism is supported by a lower horizontal rod 152 for pivoting about an axis 170. The lower horizontal rod 152 is, in turn, pivotably supported by a base 154 for pivoting about an axis 171 perpendicular to and intersecting axis 170. In a similar manner, the lower end of the vertical link 151 of the first gear linkage mechanism is supported by a lower horizontal rod 153, which is parallel to the lower horizontal rod 152 of the first gear linkage mechanism, for pivoting about an axis 172 (which is parallel to axis 170). The lower horizontal rod 153 is pivotably supported by the base 154 for pivoting about an axis 173 which is parallel to axis 171 and intersects axis 172. The base 154 is shown mounted on a support 58 like the one illustrated in FIG. 9, but the manipulator may be supported in any other convenient manner, such as in the ways described with respect to FIG. 9.

The upper end of the vertical link 150 of the first gear linkage mechanism is pivotable with respect to an upper horizontal rod 155, which is parallel to the lower horizontal rod 152 of the first gear linkage mechanism, for pivoting about an axis 174, which is parallel to axis 170. Again, in a similar manner, the upper end of the vertical link 151 of the second gear linkage mechanism is pivotable with respect to an upper horizontal rod 156, which is parallel to the lower horizontal rod 155, for pivoting about an axis 176, which is parallel to axis 172. The two upper horizontal rods 155 and 156 are pivotably connected to an upper crosspiece 157 which functions as an upper connector link (similar to the upper connector link 346 of the FIG. 7 embodiment) between the two gear linkage mechanisms. The upper horizontal rod 155 of the first gear linkage mechanism is pivotable with respect to the upper crosspiece 157 for pivoting about axis 175, which is parallel to axis 171. The upper horizontal rod 156 of the second gear linkage mechanism is pivotable with respect to the upper crosspiece 157 for pivoting about axis 177, which is parallel to axis 173.

The first gear linkage mechanism further includes a yoke 160 which is parallel to the lower horizontal rod 152. The yoke 160 is pivotably connected to the vertical link 150 between its upper and lower ends for pivoting about axis 180, which is parallel to axis 170. The second gear linkage mechanism also includes a yoke 161 which is parallel to the yoke 160 of the first gear linkage mechanism. The yoke of the second gear linkage mechanism is pivotably connected to the vertical link 151 between its upper and lower ends for pivoting about an axis 182 which is parallel to axis 172. A lower crosspiece 162, which is parallel to the upper crosspiece 157, extends between and is pivotably connected to the yokes 160 and 161. Like the upper crosspiece 157, the lower crosspiece functions as a connector link between the two gear linkage mechanisms (similar to the lower connector link 348 of the FIG. 7 embodiment). The lower crosspiece 162 is pivotable with respect to the yoke 160 of the first gear linkage mechanism about axis 181, which is parallel to axis 171. Similarly, the lower crosspiece 162 is also pivotable with respect to the yoke 161 of the second gear linkage mechanism about axis 183, which is parallel to axis 173. The upper and lower crosspieces 157, 162 constrain the vertical links 150, 151 of the two gear linkage mechanisms such that the vertical links remain in parallel relation as they respectively pivot about axis 171 and axis 173.

For supporting a tool 166, the manipulator illustrated in FIGS. 17–23 includes a tool holder link 165 which is connected to the two gear linkage mechanisms via extended portions 158, 163 of the upper and lower crosspieces. Specifically, the extended portion 158 of the upper crosspiece 157 has a yoke 159 at its free end. The yoke 159 is pivotably connected to the extended portion 158 for pivoting about an axis 184, which is parallel to axis 171. The yoke 159 is also pivotably connected to the tool holder link 165 for pivoting about an axis 185 which is perpendicular to axis 184. The extended portion 163 of the lower crosspiece 162 extends parallel to the extended portion 158 of the upper crosspiece and pivotally supports a yoke 164 at its free end for rotation about axis 186, which is parallel to axis 184. The yoke 164 is also pivotably connected to the tool support link 165 for pivoting about axis 187, which is perpendicular to axis 186 and parallel to axis 185.

The upper horizontal rod 155, 156 of each gear linkage mechanism is constrained to move in parallel relation to the lower horizontal rod 152 and 153 of each mechanism by a gear train comprising an odd number of gears. In the 20 illustrated embodiment, each gear linkage mechanism includes three gears 200–202, 205–207. On the vertical link 150 of the first gear linkage mechanism, a first lower gear 200 is secured to the lower horizontal rod 152. The lower gear 200 is concentric with respect to axis 170 so that the vertical link 150 can rotate with respect to the lower gear 200 about axis 170. A second upper gear 201 is secured to the upper horizontal rod 155 concentrically with axis 174 and is rotatable with respect to the vertical link 150 about axis 174. A third intermediate gear 202 is pivotably mounted on the vertical link 150 between and in mesh with the upper and lower gears 201 and 202. The rotational axis of the intermediate gear 202 is shown coinciding with axis 180, but the location of its rotational axis is not critical. Lower, upper and intermediate gears 205–207 are mounted on the vertical link 151 of the second gear linkage mechanism in the same manner. The reduction ratios of the gears are selected so that, for example, when the vertical link 150 of the first gear linkage mechanism pivots with respect to the lower horizontal rod 152 about axis 170 in a first rotational direction by an angle α, the upper horizontal rod 155 will rotate with respect to link 150 about axis 174 in the opposite rotational direction by the same angle a. Thus, the lower and upper horizontal rods 152, 155 of the first gear linkage mechanism remain parallel to each other. The reduction ratios of the gears 205–207 for the second gear linkage mechanism are selected in a similar manner.

Figure 17:
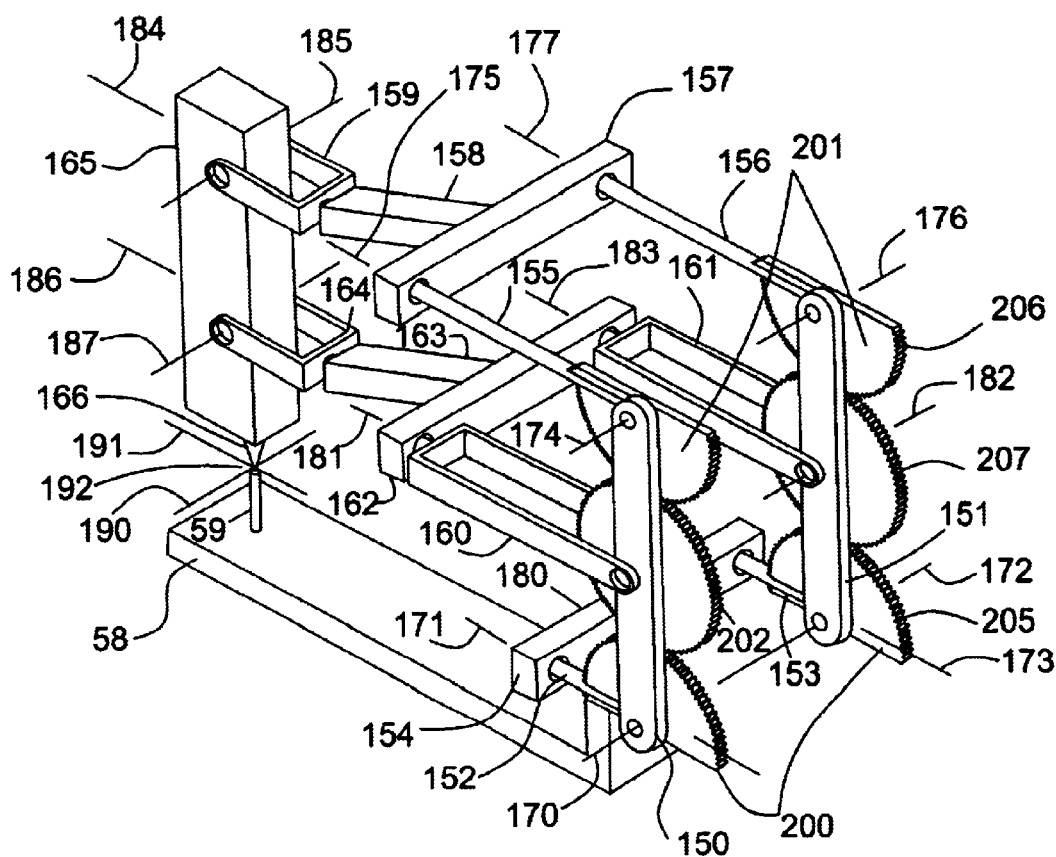
FIG. 17 is an isometric view of another embodiment of a manipulator according to the present invention.
Figure 18:
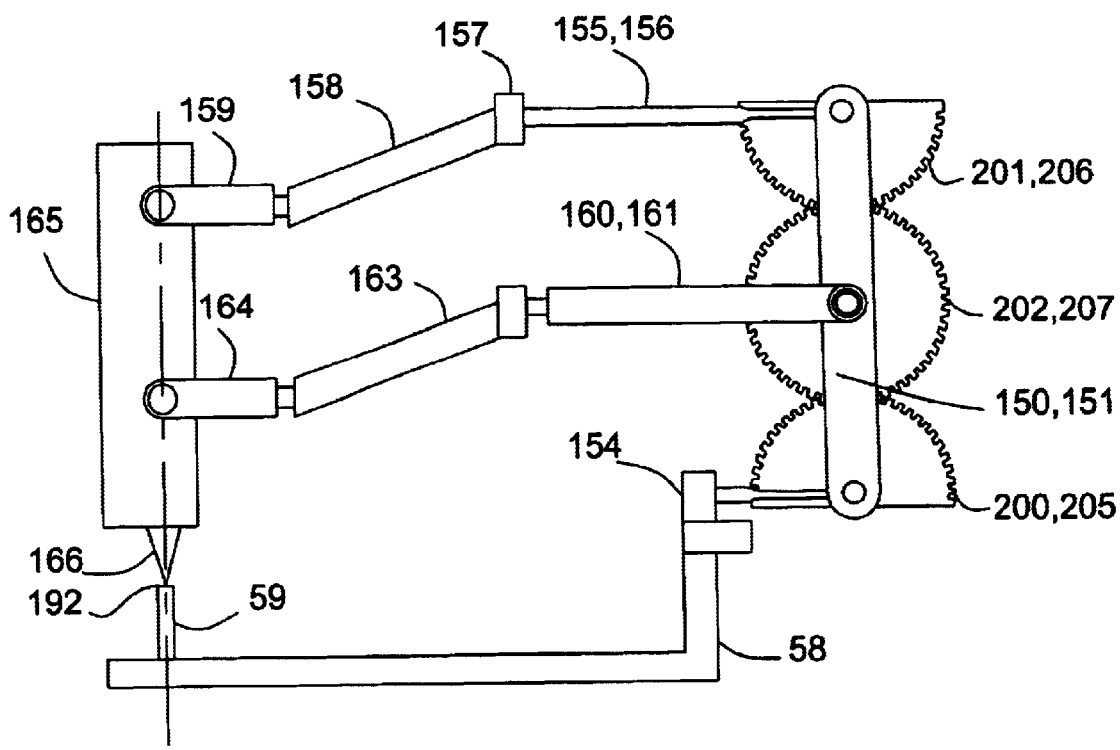
FIG. 18 is a side elevation of the embodiment of FIG. 15.
Figure 19:
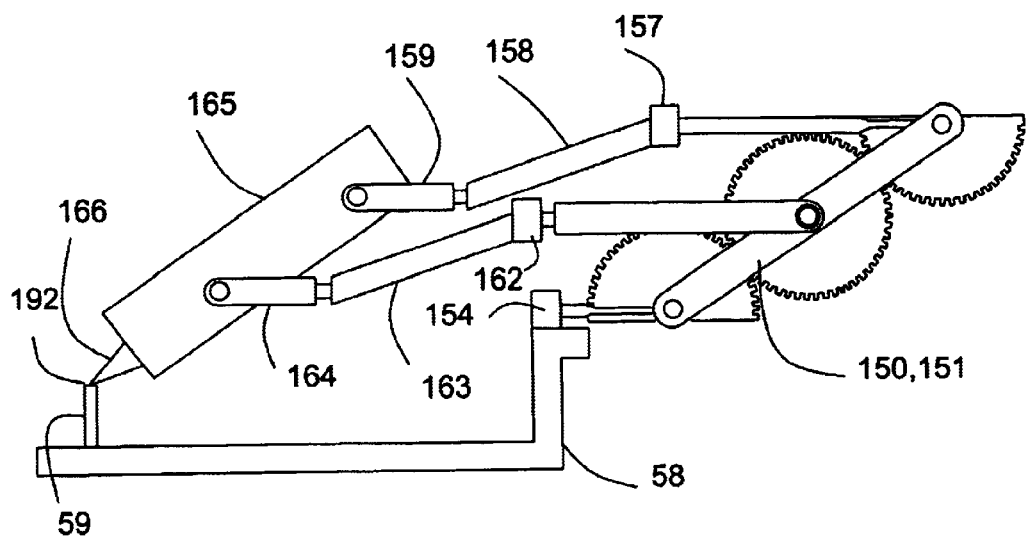
FIGS. 19 and 20 are respectively a side elevation and an isometric view of the embodiment of FIG. 18 rotated backwards from the position shown in FIG. 18.
Figure 20:
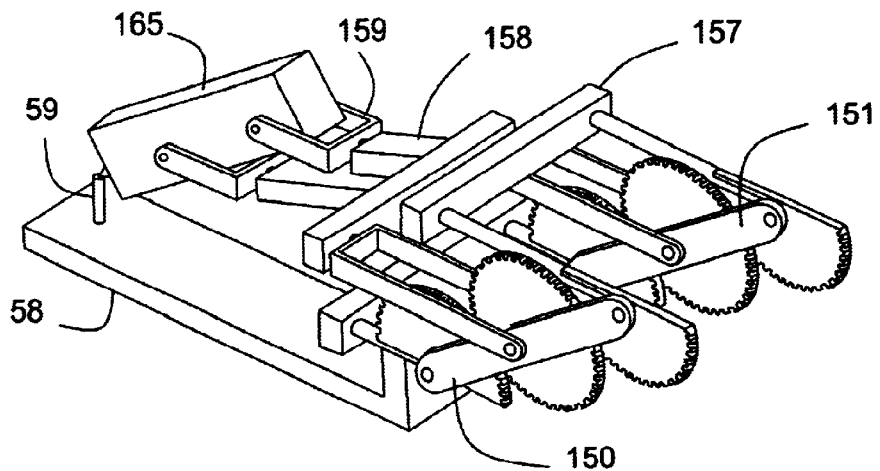
Figure 21:
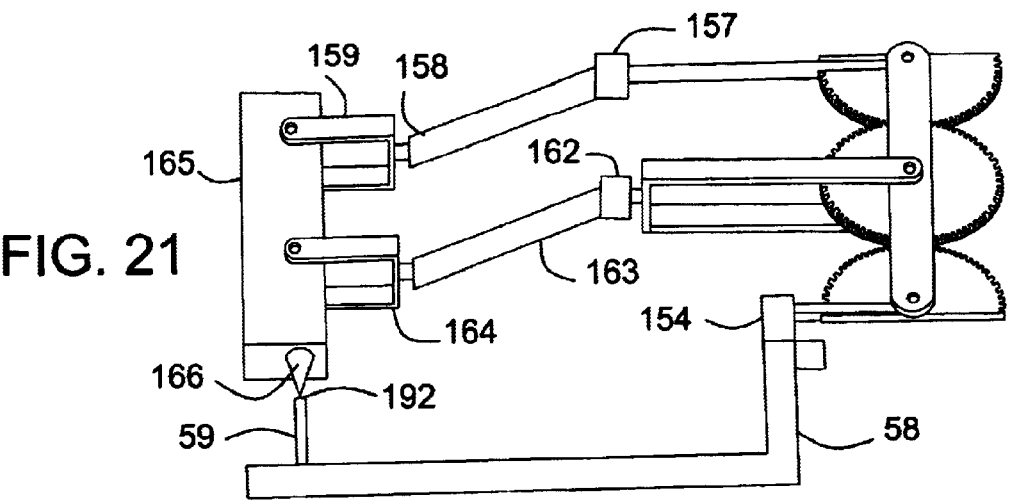
FIGS. 21, 22, and 23 are respectively a side elevation, an isometric view, and a front elevation of the embodiment of FIG. 18 rotated sideways from the position shown in FIG. 18.
Figure 22:
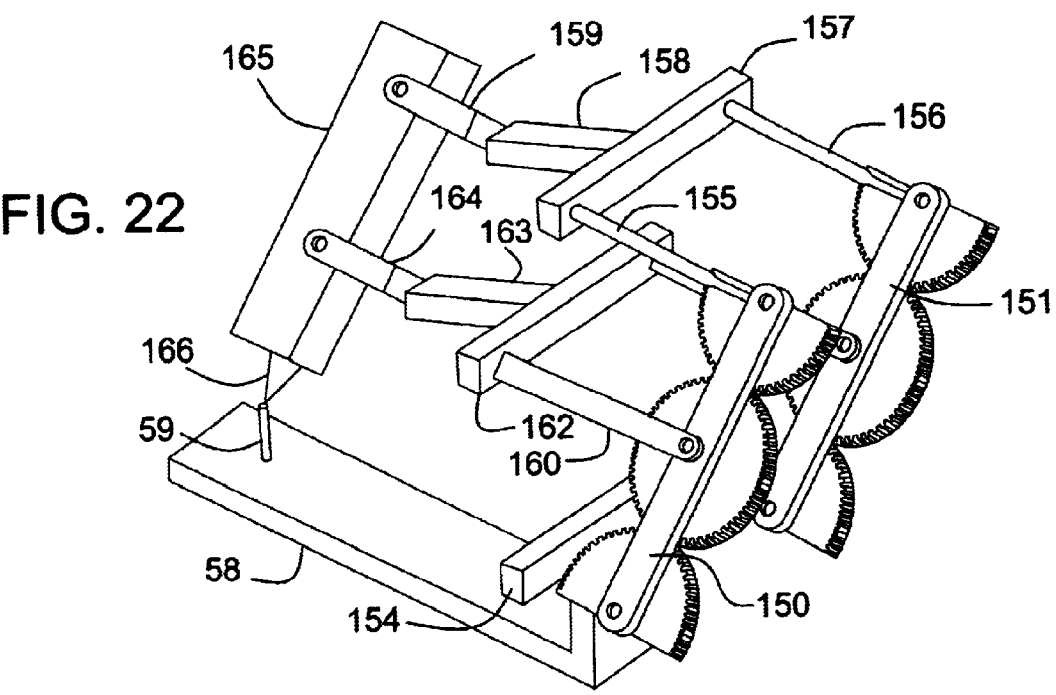
Figure 23:
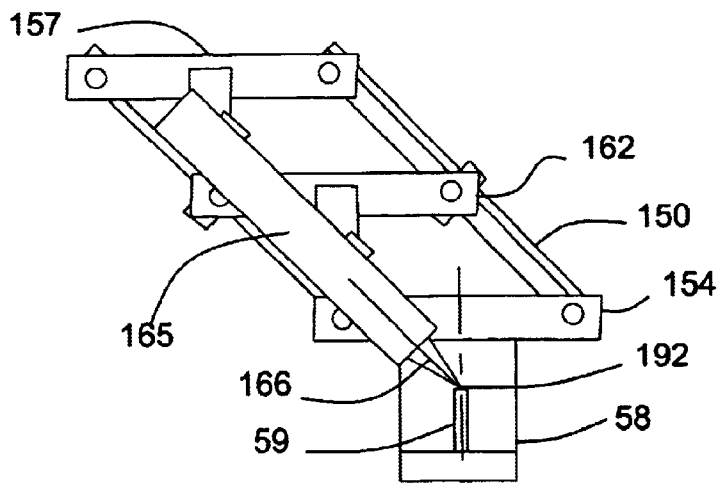

As shown in FIG. 19, which is a side elevation of the manipulator of FIG. 17 pivoted backwards from the position shown in FIG. 17, pivoting the vertical links of the two gear linkage mechanisms about axes 170 and 172 causes the tool holder link 165 and the tool 166 to pivot at a virtual pivot point 192 about an axis 190 spaced from a plane containing axes 171 and 172. In this respect, the manipulator shown in FIG. 17 functions similar to the embodiment shown in FIG. 2 with the vertical links 150, 152 of the parallel gear linkage mechanisms functioning as a single link and the gear trains performing the function of maintaining the upper and lower horizontal rods in parallel relation. When the vertical links 150 and 151 are simultaneously pivoted side-to-side about axes 171 and 173, as shown, for example, in FIGS. 21–23, the tool holder link 165 and the tool 166 pivot at the virtual pivot point 192 about an axis 191 which is perpendicular to and intersects axis 190 at the virtual pivot point 192. Thus, the tool 166 can be pivoted with two rotational degrees of freedom about the virtual pivot point 192. When performing the side-to-side movement, the manipulator can be considered like the kinematic model of FIG. 7, with the vertical links 150 and 151 functioning like links 41 and 42 of FIG. 7, the upper and lower crosspieces 157 and 162 functioning like links 43 and 44 of FIG. 7, the extended portion of the upper crosspiece 158 and its yoke 159 functioning like link 51 of FIG. 7, the extended portion of the lower crosspiece 163 and its yoke 164 functioning like link 52 of FIG. 7, and the tool holder link 165 functioning like link 53 of FIG. 7. As will be appreciated, the manipulator of FIGS. 17–23 can be driven by hand or by a motor or other actuator in a manner similar to that described with respect to FIG. 16.

In FIGS. 17–23, the upper and lower gears 200, 201, 205, and 206 of the two gear linkage mechanisms are in the form of sectors of a circle. Each of the intermediate gears 202 and 207 is in the form a complete circle. However, the upper and lower gears may also be completely circular, and the intermediate gears 202 and 207 may each comprise sectors instead of a complete circle. In the illustrated embodiment, the gears of each gear train have the same diameter. However, the gears can have different diameters as long as the rotational angle of the upper gear 201 and 206 of each gear linkage mechanism is equal and opposite to the rotational angle of the lower gears 200 and 205 of each gear linkage mechanism when the vertical links 150 and 151 rotate with respect to the lower gears. For example, the upper and lower gears may have the same diameter, and the intermediate gear may have a different diameter. In addition, the number of gears on each link is not limited to three. In general, any odd number of gears greater than or equal to three can perform the desired function.

Figure 24:
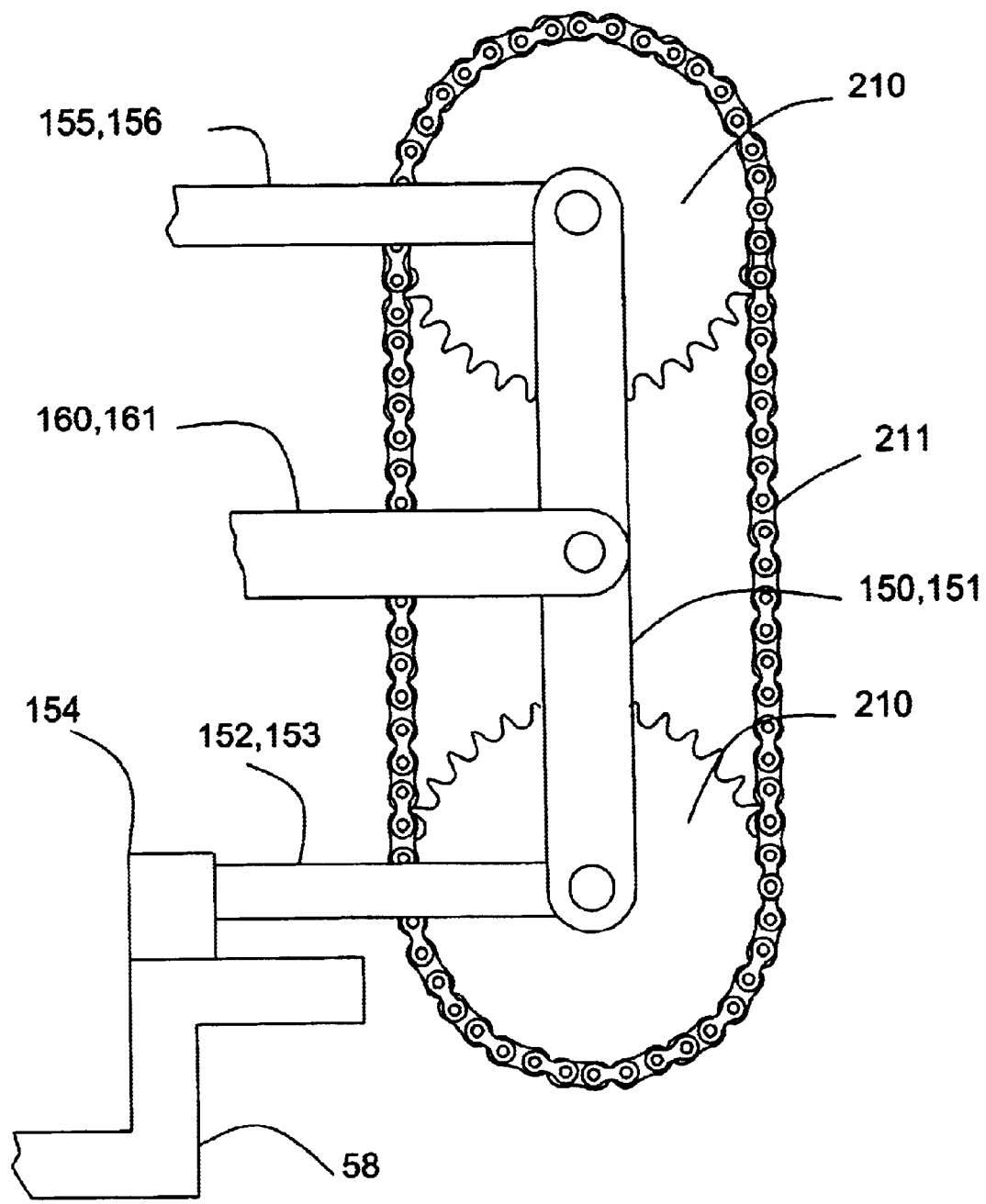
FIGS. 24 and 25 are schematic side elevations of links equipped with different means for maintaining the attitude of links from that shown in FIG. 18.
Figure 25:
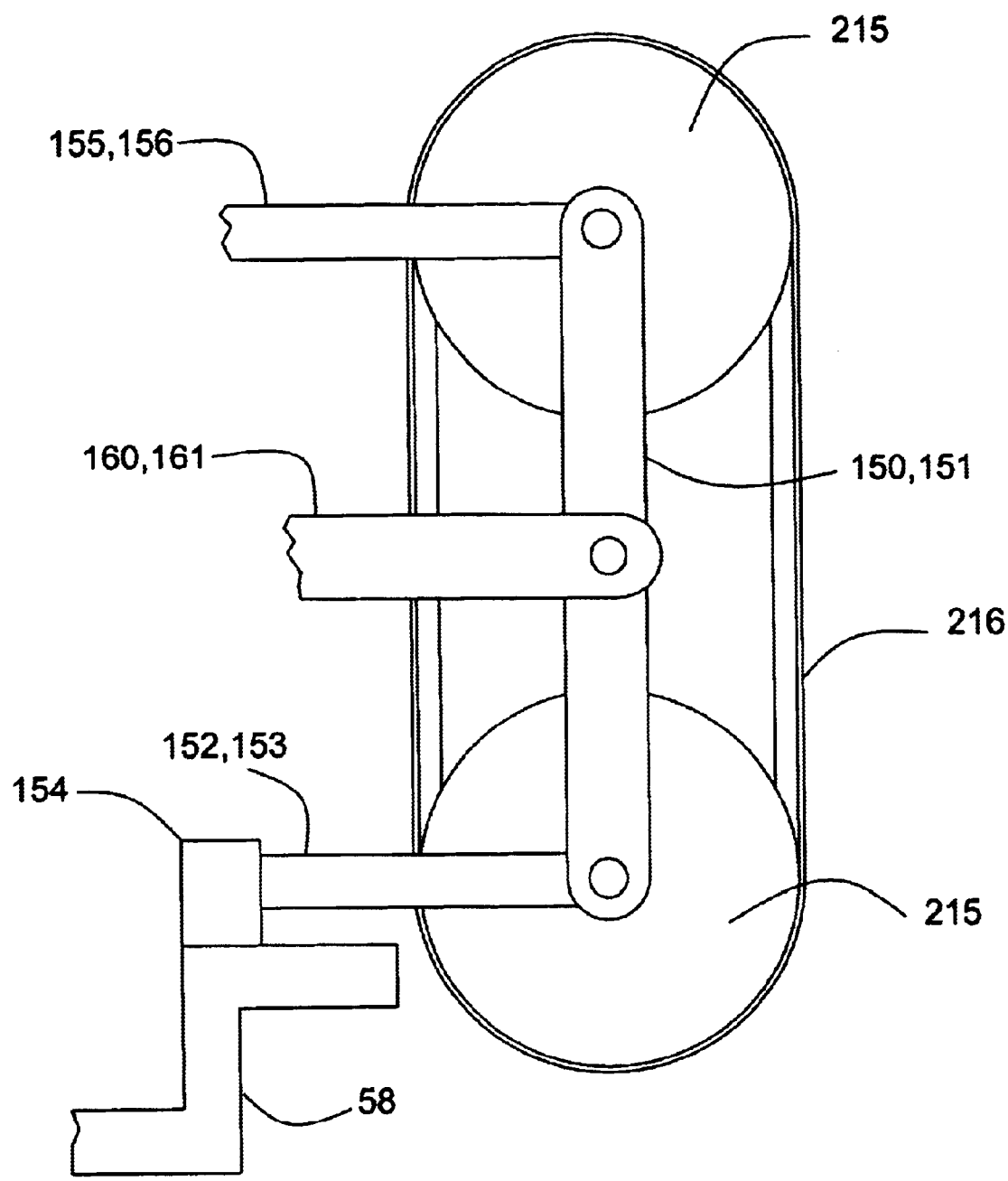

Mechanisms other than gears can be used to constrain, for example, the upper and lower horizontal rods 155 and 152 of the manipulator shown FIG. 17 to move in parallel relation. For example, the gears can be replaced by rollers that are in rolling contact with each other. Alternatively, the intermediate gear 202 on the vertical link may be omitted, and the upper and lower gears can be replaced by sprockets 210 connected to each other by a chain 211 so as to produce a parallel chain linkage mechanism, as shown in FIG. 24, or by pulleys 215 connected to each other by a belt or cable 216 so as to produce a parallel mechanical belt or cable linkage mechanism, as shown in FIG. 25. In FIG. 24, a lower sprocket 210 is secured to the lower horizontal rod 152, 153 of each parallelogram mechanism, and an upper sprocket 210 is secured to the upper horizontal rod 155, 156 of each parallelogram mechanism. The lower end of the vertical link 150, 151 of each parallelogram mechanism is pivotable with respect to the corresponding lower sprocket 210, and the upper end of the vertical link 150, 151 is pivotable with respect to the corresponding upper sprocket 210. In FIG. 25, a lower pulley 215 is the lower horizontal rod 152, 153 of each parallelogram mechanism, and an upper pulley 215 is secured to the upper horizontal rod 155, 156 of each parallelogram mechanism. The lower end of the vertical link 150, 151 of each parallelogram mechanism is pivotable with respect to the corresponding lower pulley 215, and the upper end of the vertical link 150, 151 is pivotable with respect to the corresponding upper pulley 215.

Figure 26:
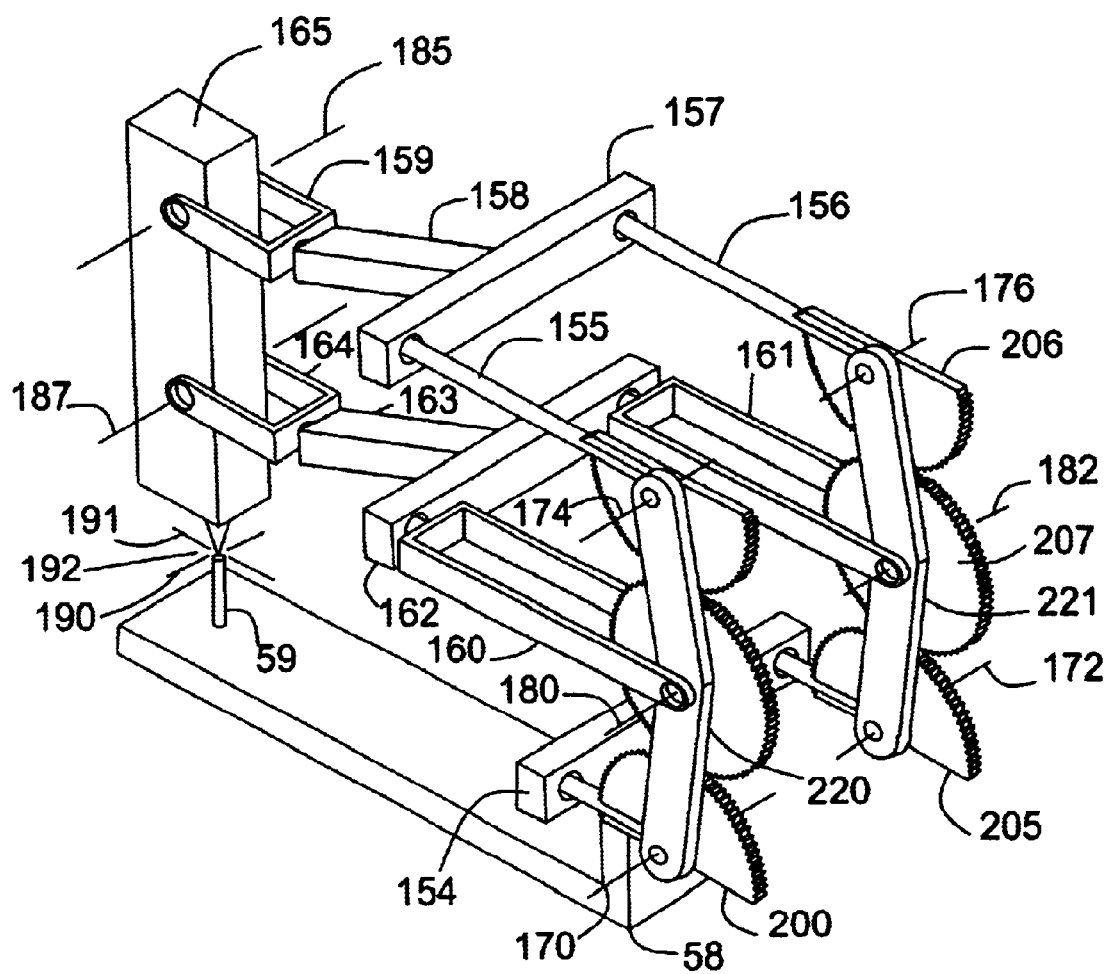
FIG. 26 is an isometric view of another embodiment of a manipulator according to the present invention.
Figure 27:
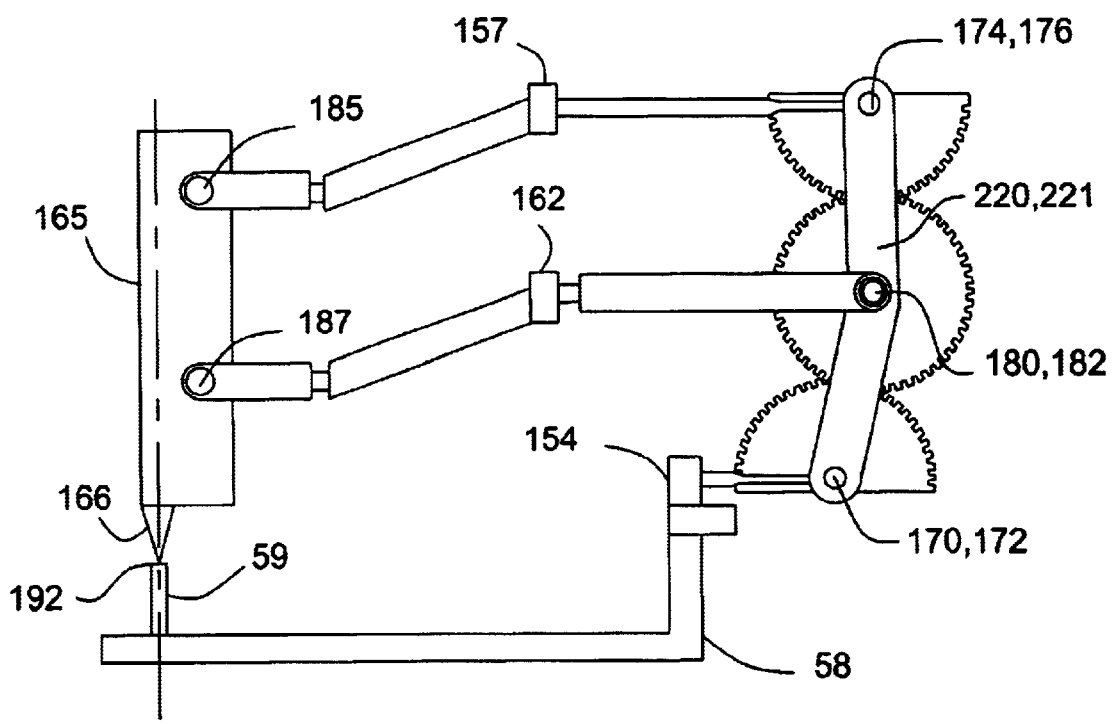
FIG. 27 is a side elevation of the embodiment of FIG. 26.

With the manipulator embodiment shown in FIG. 17, the pivot axes 170, 172, 174, 176, 180, and 182 associated with the vertical link of each parallelogram mechanism lie in the same plane, so the virtual pivot point 192 is aligned with a plane containing axes 185 and 187. A variation of the FIGS. 17–23 embodiment is shown in FIGS. 26 and 27. With the embodiment of the invention shown in FIGS. 26 and 27, the vertical links 150 and 151 of FIG. 17 have been replaced by vertical links 220, 221 which have a shape such that axes 180 and 182 are spaced from a plane containing the other rotational axes 170, 172, 174, and 176 associated with the vertical links. The arrangement of the various links and rods is otherwise the same as in FIG. 17. Similar to the embodiment shown in FIG. 6, this shape of the vertical links 220 and 221 enables the virtual pivot point 192 to be spaced from a plane containing the axes 185 and 187 defined by the pivotal connections of the yokes 159, 164 of the extended portions 158, 163 of the upper and lower crosspieces 157, 162 to the tool holder link 165. Accordingly, the tool 166 can be mounted on the tool holder link 165 in a location other than a plane containing axes 185 and 187 and still contact the virtual pivot point 192. For example, the tool 166 can be mounted such that it is spaced forward of the plane containing axes 185 and 187 so that it does not interfere with imaging operations and where the yokes 159 and 164 or other portions of the manipulator do not interfere with movement of the tool 166.

Figure 28:
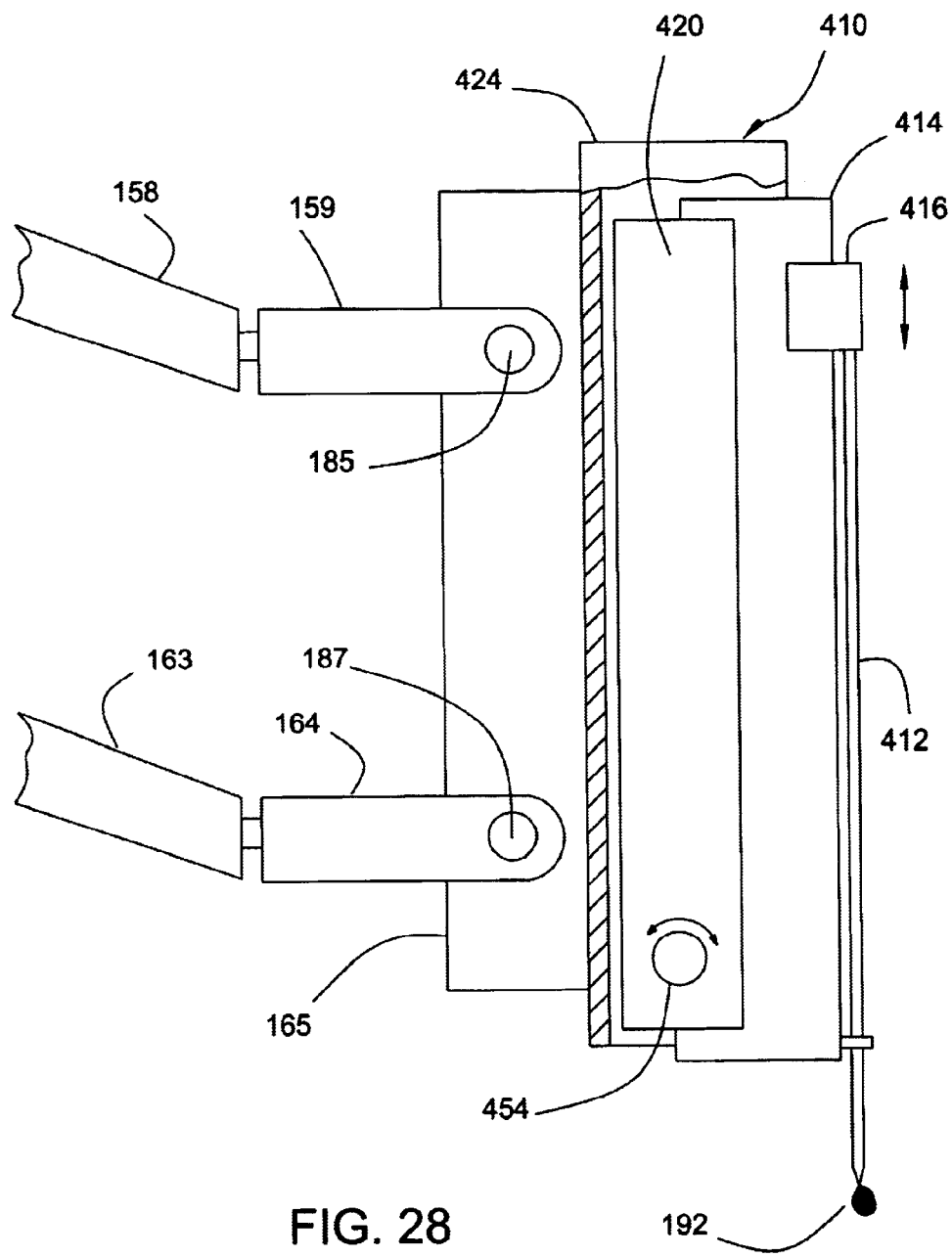
FIG. 28 is a side elevation of a portion of the embodiment of FIG. 26 supporting a tool holder.

In accordance with a further aspect of the present invention, the manipulator can include a tool holder 410 for holding and moving a tool with one or more degrees of freedom while minimizing contact between the tool holder and the tool. As stated above, a tool which is supported by a manipulator according to the present invention can be selected from a wide variety of devices, both for medical and non-medical purposes. FIG. 28 illustrates a portion of a manipulator according to the present invention having the structure shown in FIG. 26 which includes a tool holder 410 configured to hold a biopsy needle 412. The tool holder 410 is mounted on the link 165 and can translate the needle 412 in its lengthwise direction with respect to the link 165.

Figure 29:
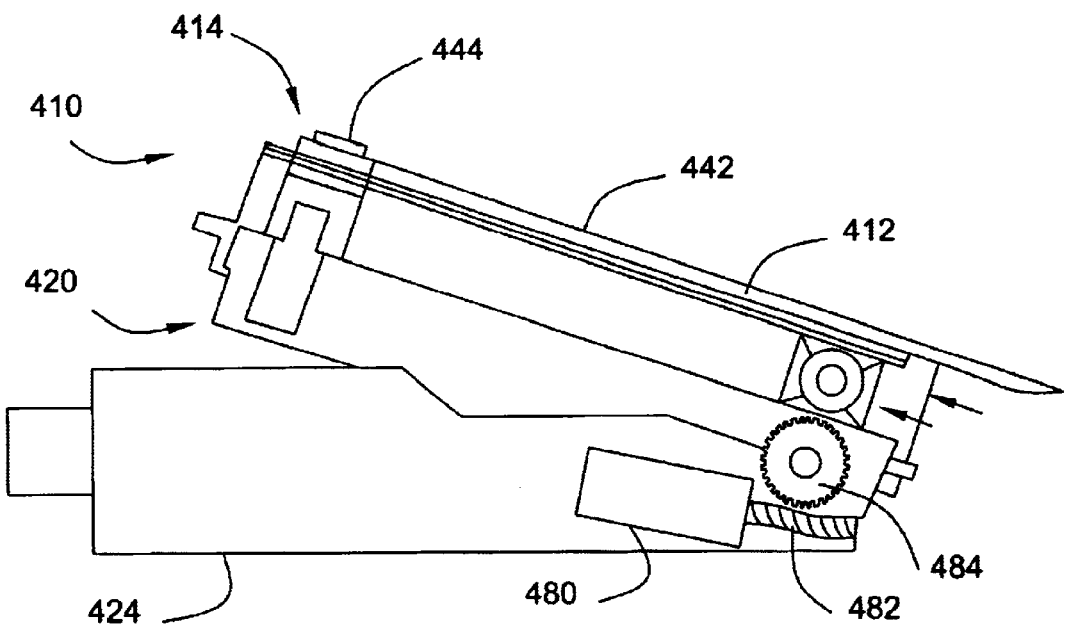
FIG. 29 is a side elevation view of an embodiment of the tool holder of FIG. 28.
Figure 30:
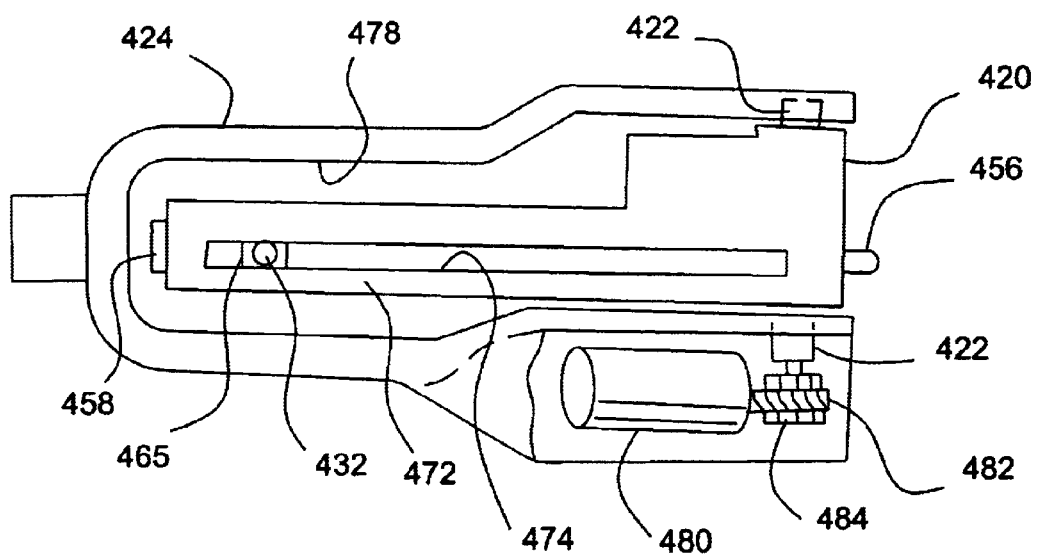
FIG. 30 is a top view of the tool holder of FIG. 29 with the cartridge removed.

To this end, as shown in FIGS. 28–30, the tool holder 410 includes a cartridge 414 having a movable carriage 416 which can engage the proximal end of the needle 412 and can move in the lengthwise direction of the needle to translate it toward or away from a patient. The cartridge 414 is detachably mounted on a drive unit 420 which contains a motor or other drive mechanism which can be operatively coupled to the carriage 416 to translate the carriage in the lengthwise direction of the needle 412. The drive unit 420 includes a pair of aligned shafts or axles 422 which are pivotably supported by a yoke 424 secured to link 165. The yoke 424 includes a motor or other drive mechanism which can controllably pivot the drive unit 420 about the rotational axes of the axles 422 to a desired angle. However, when the tool holder 410 is used with a manipulator according to the present invention, the motor is typically not operated so that the drive unit 420 remains at a constant angle with respect to the yoke 424, with the longitudinal axis of the needle 412 aligned with the virtual pivot point 192 of the manipulator.

The illustrated tool holder 410 is just one example of many possible devices for supporting a needle, but it is particularly advantageous because it minimizes the number of components which are subject to contamination during a medical procedure using the needle 412. In particular, the only portion of a tool holder according to the present invention which comes into direct contact with a needle or other medical tool is the replaceable cartridge. The motors for translating the carriage 416 or for rotating the drive unit 420 are protected from contamination, so the drive unit and the yoke 424 typically do not need to be sterilized between uses. On the other hand, the cartridge 414 and the needle 412, which may be subject to contamination, can be readily replaced as a single unit after a single use, to be either sterilized or discarded. The cartridge does not require high precision for its manufacture nor does it require high strength, so it can be inexpensively manufactured to enable it to be economically discarded, if desired, after a single use. The other portions of the tool holder are substantially free from contamination, so they can be reused with a new cartridge without having to be sterilized between uses.

Figure 33:
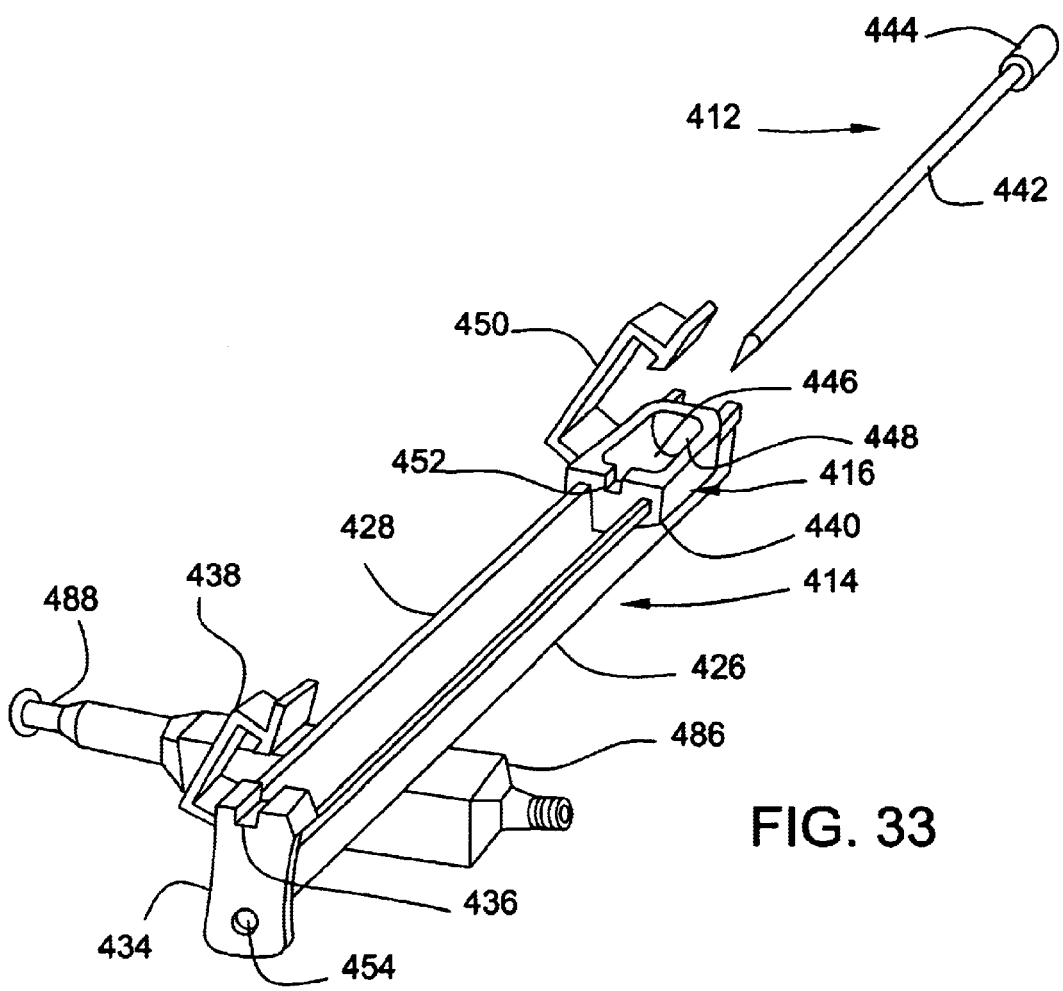
FIG. 33 is an enlarged transverse cross-sectional view of the carriage guide of the cartridge of FIG. 31.
Figure 34:
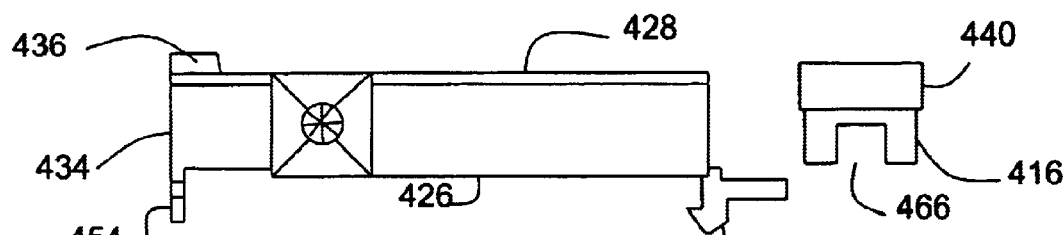
FIG. 34 is a plan view of the carriage drive unit of the tool holder of FIG. 29 with the cover of the drive unit shown in phantom.
Figure 35:
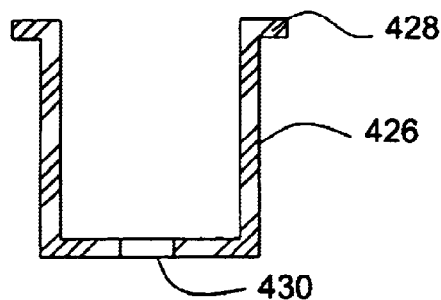
FIG. 35 is a side elevation of the carriage drive unit of FIG. 34.

As shown in FIGS. 33–35, the cartridge 414 includes an elongated carriage guide 426 along which the carriage is movable in a linear path in a lengthwise direction of the guide. The illustrated carriage guide 426 has a generally U-shaped transverse cross section with two elongated guide flanges 428 extending transversely from its upper end as shown in FIG. 35. The carriage guide 426, however, may have any desired shape which enables it to guide the carriage 416. An elongated slot 430 through which a drive pin 432 of the drive unit 420 can pass extends in the lengthwise direction of the bottom surface of the carriage guide 426. An end plate 434 is secured to the lower end (the end closest to a patient during use) of the carriage guide 426 as shown in FIGS. 33 and 34.

The end plate 434 includes a needle guide for guiding a portion of the needle 412 as it translates along the carriage guide 426. The illustrated needle guide comprises a notch 436 formed in the end plate 434 through which the needle 412 can slidably pass. The notch 436 may be equipped with a retainer such as a clip 438 which can pivot between an open position in which the needle 412 can be easily inserted into or removed from the notch 436 and a closed position in which the clip 438 prevents the removal of the needle 412 from the notch 436.

The carriage 416 can have any shape which enables it to translate along the carriage guide 426 while engaging a needle 412 or other medical tool. The illustrated carriage 416 has a pair of flanges 440 at its open end extending in its lengthwise direction which are shaped to fit around the guide flanges 428 on the carriage guide 426 to permit the carriage 416 to slide along the carriage guide 426 along a linear path. The carriage 416 can engage the needle 412 so as to be capable of exerting a drive force on the needle 412 in its lengthwise direction to insert the needle 412 into or retract it from a patient's body.

The manner in which the carriage 416 engages the needle 412 can be chosen in accordance with the structure of the needle. As shown in FIG. 33, the illustrated needle 412 is a commercially available introducer needle including an elongated hollow shank 442 and an engaging portion in the form of an enlarged head 444 molded around or otherwise secured to the proximal end (the end remote from a patient) of the shank. The illustrated carriage 416 is adapted to hold the needle 412 by its head 444. The carriage 416 includes a recess 446 which is sized to receive the head 444 of the needle 412. The lengthwise end walls 448 of the recess 446 can press against the end faces of the head 444 of the needle 412 to exert a force on the head in the lengthwise direction of the needle. Alternatively, the side walls of the recess 446 may fit snugly around the head 444 to transmit a force to the head in the longitudinal direction of the needle 412 by friction.

A retainer in the form of a clip 450 on the carriage 416 can be pivoted between an open position shown in FIG. 33 in which the needle 412 can be installed on or removed from the carriage and a closed position in which the clip 450 fits over the head 444 of the needle 412 to resist removal of the needle. One of the end walls 448 of the carriage 416 includes a notch 452 communicating with the recess 446 through which the shank 442 of the needle 412 can pass. The carriage 416 may hold the needle 412 in any other suitable manner. For example, it may include jaws or fingers which can grasp either the shank 442 or the head 444 of the needle 412. As another example, if the head 444 of the needle 412 has a varying outer diameter, a reduced diameter portion of the head may be disposed in the notch 552, and portions of larger diameter adjoining the reduced diameter portion may be disposed outside of the notch on either side of it to prevent lengthwise movement of the needle 412 with respect to the carriage 416, with one of the larger diameter portions disposed in the recess 446 and the other disposed outside the recess. If the needle 412 is intended to house another member, such as an obturator, the recess 446 may be made large enough to receive a head or other portion of the member housed in the needle.

As will be appreciated by those skilled in the art, when a different type of tool is being held by the tool holder 410, the carriage 416 may be modified to engage the tool in a different manner from that shown in the figures. However, the illustrated arrangement can be used for any tool having an elongated shank and an enlarged engagement portion, such as a head, hub, collar, flange, or knob attached to the shank. Moreover, the cartridge can be adapted to permit the tool to be released after the tool is set in a particular position.

The cartridge 414 is preferably readily detachable from the drive unit 420 to permit the cartridge to be easily installed and replaced. Any convenient method of attaching the cartridge 414 to the drive unit 420 can be employed. In the illustrated cartridge 414, the end plate 434 is equipped with a hole 454 through which an engagement pin 456 of the drive unit 420 (FIG. 31) can pass. An elastically deformable clip 460 which can detachably engage a flange 458 on the opposing end of the drive unit 420 (FIGS. 31 and 32) is mounted on the opposite end of the carriage guide 426.

In order to prevent the cartridge 414 from being reused with more than one patient by simply replacing the needle 412 without the cartridge being sterilized, the cartridge may be structured so that a needle cannot be removed from the cartridge without rendering the cartridge unusable. For example, one or both of the clips 438 and 450 for retaining the needle 412 in the cartridge 414 may engage the cartridge when the clip is in its closed position in a manner such that a portion of the clip or a portion of the cartridge breaks off when the clip is opened, making it impossible to again secure the clip in a closed position and secure the needle to the cartridge. Such a breakable portion may be in the form of a flange, a claw, a head, etc., which is snap-engageable with another member when the clip is in its closed position and which breaks off when the clip is opened.

Figure 31:
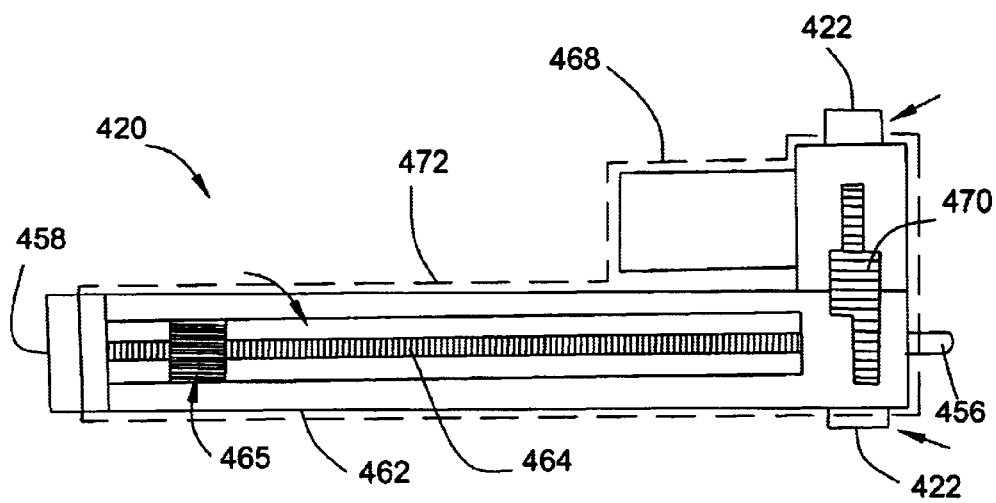
FIG. 31 is a isometric view of the cartridge of FIG. 29 with a needle removed.
Figure 32:
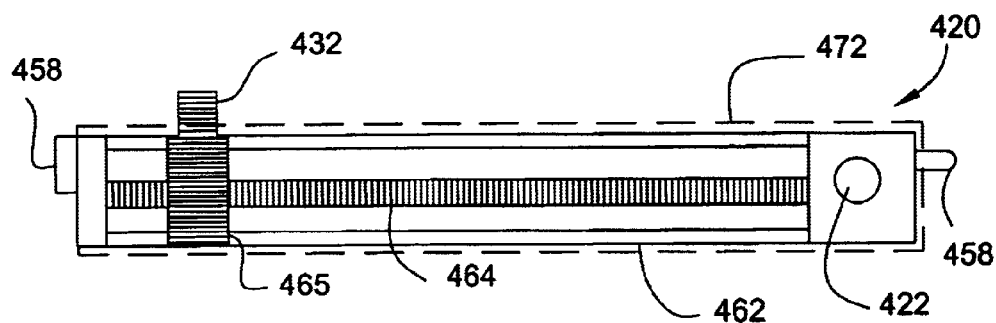
FIG. 32 is a side elevation of the cartridge of FIG. 29 in a partially disassembled state.

The drive unit 420 can have any structure which enables it to exert a drive force on the carriage 416 in a lengthwise direction of the needle 412 to cause the carriage to translate along the carriage guide 426. As shown in FIGS. 31–32, the illustrated drive unit 420 includes a frame 462 which supports a drive mechanism. The illustrated drive mechanism includes a lead screw 464 which engages with a movable nut 465 having a drive pin 432 projecting from its upper surface for detachable engagement with the carriage 416. The carriage 416 may engage the pin 432 on the drive unit 420 in any convenient manner. In the illustrated embodiment, the carriage 416 includes a recess 466 in its bottom surface for engagement with the pin 432. The nut 465 can be prevented from rotating as it translates along the lead screw 464 by the sides of the frame 462 or by a guide member, such as a rod, slidably engaging with the nut 465. The lead screw 464 can be rotated about its axis by any suitable drive source, such as by an electric motor 468 drivably connected to the lead screw 464 by a gear unit 470. When the motor 468 is driven, the lead screw 464 is rotated about its axis to translate the nut 465 along the lead screw 464 and move the carriage 416 of the cartridge 414 either toward or away from a patient's body. A few examples of other suitable drive mechanisms for translating the carriage 416 along the carriage guide 426 include a belt and pulley drive, a linear motor, or a pneumatic or hydraulic cylinder.

The moving parts of the drive unit 420 are preferably enclosed to protect them from contamination and to prevent them from contaminating a patient. As shown in FIG. 30, the illustrated drive unit 420 includes a cover 472 which surrounds all the moving parts except for the pin 432 of the nut 465, which extends through an elongated slit 474 in the top surface of the cover parallel to the lead screw 464. The portion of the cover 472 in which the slit 474 is formed may be made of a flexible material so that the slit is substantially closed except in the region immediately surrounding the pin 432 where the pin forces the slit 474 open.

The drive unit 420 is preferably pivotably supported by the yoke 424 for pivoting about a pitch axis which is transverse (e.g., perpendicular) to the axis of the needle 412. The illustrated yoke 434 includes a pair of legs 476 separated by a cavity 478 for receiving the drive unit 420 when the drive unit is in an initial position ash shown in FIG. 30. The drive unit 420 may be pivoted about the pitch axis manually, or the yoke 424 or the drive unit may be equipped with a drive mechanism for exerting a rotary drive force on the drive unit about the pitch axis. For example, the illustrated yoke 424 is equipped with an electric motor 480 (FIGS. 29 and 30) which is operatively connected to one of the axles 422 of the drive unit 420 by a gear unit, such as a worm gear unit including a worm 482 secured to the output shaft of the motor 480 and a worm gear 484 secured to the axle 422. When the motor 480 is operated, the entire drive unit 420 can be pivoted about the pitch axis to a desired angle. In FIG. 29, the drive unit 420 is shown pivoted clockwise about the pitch axis so that the proximal end of the needle 412 is raised above the yoke 424, but the drive unit may be rotated in the opposite direction so that the proximal end of the needle 412 is positioned below the yoke. The drive unit can have any desired range of rotation about the pitch axis. The greater the range of rotation about the pitch axis, the less the entire tool holder 410 needs to be moved to obtain a desired angle of the needle 412 with respect to a patient's body. In the present embodiment, the drive unit can be rotated about the pitch axis by approximately ±115° from its initial position (i.e., with the needle parallel to the longitudinal axis of the yoke), but a greater range of rotation may be employed. For example, the drive unit 420 may be rotatable by 360° around the pitch axis.

In some situations, it may be convenient to dispense a drug or other substance to a patient during use of the needle 412. Therefore, the cartridge 414 may be equipped with one or more devices for dispensing a local anesthetic, an antiseptic agent, or other substance to a patient when the needle 412 is being inserted into the patient's body. As shown in FIG. 33, the illustrated cartridge 414 is equipped with first and second dispensing units 486 and 488 disposed on opposite widthwise sides of the carriage guide 426 near the end plate 434. The dispensing units, however, can be mounted in any convenient location on the cartridge, drive unit or yoke. The first dispensing unit 486 comprises an applicator for applying a liquid to the skin of a patient, while the second dispensing unit 488 comprises an injector for administering a percutaneous injection of a substance to a patient.

Figure 36:
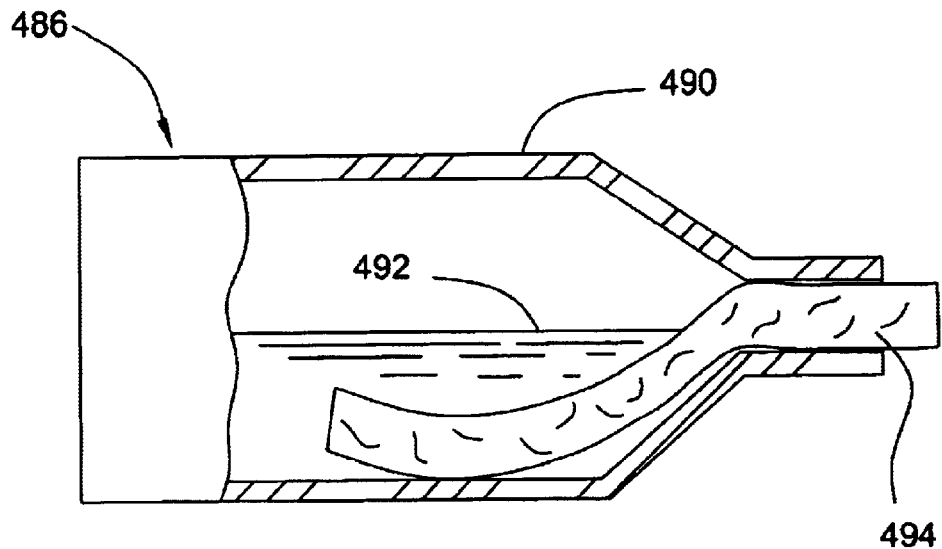
FIGS. 36 and 37 are longitudinal cross-sectional views of the dispensing units of the cartridge of FIG. 31.
Figure 37:
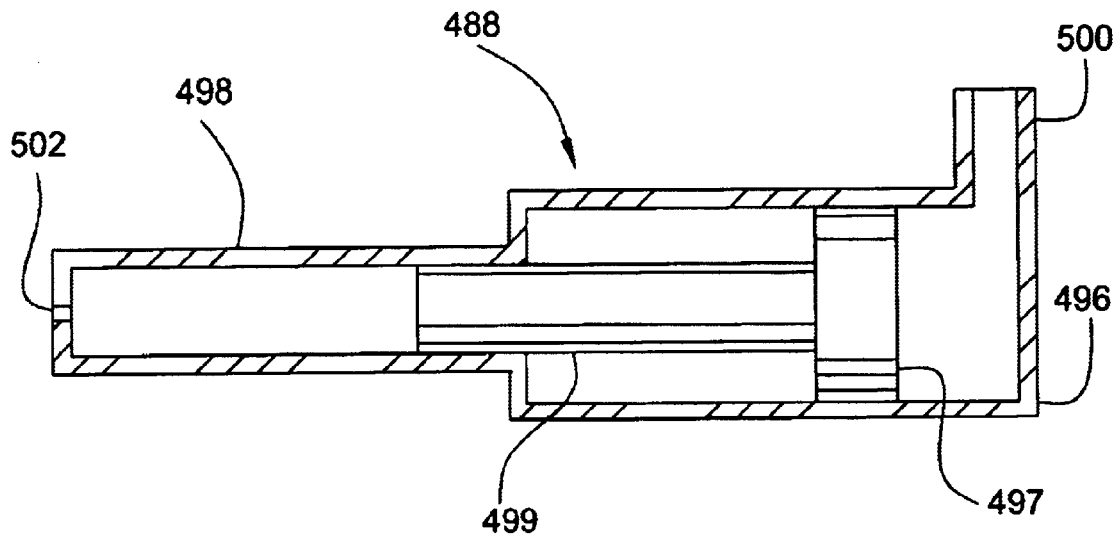

FIGS. 36 and 37 are schematic cross-sectional views of examples of the two dispensing units 486 and 488, respectively. As shown in FIG. 36, the first dispensing unit 486 includes a reservoir 490 containing a liquid 492 to be applied to a patient's skin. An absorbent wick 494 extends from the interior of the reservoir 490 where it contacts the liquid 492 through an opening 495 of the reservoir 490 to its exterior. When not in use, the outer end of the wick 494 may be covered by a cap or other suitable member to prevent it from drying out. The liquid 492 is drawn by the wick 494 to the outer end of the wick, which can be placed against a patient's skin to transfer the liquid 492 from the reservoir 490 to the skin, and the tool holder 410 can be moved along a desired path to swab the patient's skin with the liquid. The liquid 492 in the reservoir 490 can be any substance suitable for topical application. For example, it may be PVD iodine or other antiseptic agent for use in cleansing a patient's skin in the region into which the needle 412 is to be inserted. Devices other than a wick 494 can be used to transfer liquid 492 from the reservoir 490 to the patient's skin in a gradual manner, such as a roller ball similar to that used in a ballpoint pen or a spring-loaded valve which can open when pressed against the patient's skin.

As shown in FIG. 37, the second dispensing unit 488 includes a housing having a first chamber 496 containing a first movable piston 497 and a second chamber 498 adjoining the first chamber 496 and containing a second movable piston 499 coupled to the first piston 497 so that the two pistons can move together. The first chamber 496 is equipped with a fluid port 500 through which a drive fluid can be introduced under pressure into the first chamber. The second chamber 498 is equipped with an orifice 502 opening onto the exterior of the housing through which a fluid to be administered to a patient can be discharged under pressure. When not in use, the orifice 502 may be closed by a cap, a stopper, sealing tape, or other suitable member to prevent fluid from leaking from the second chamber 498. The drive fluid for driving the first piston 497 can be either a gas or a liquid, a few examples of suitable drive fluids being air, $CO_2$, and water.

Prior to use, the second chamber 498 is filled with a fluid (usually a liquid but possibly a gas) to be administered to a patient, which may be any substance suitable for percutaneous injection during a medical procedure involving a needle 412 or other medical tool. For example, the fluid may be Lidocaine or other local anesthetic for preventing pain in the region into which the needle is to be inserted. To inject the fluid into a patient, the cap or other cover is removed from the orifice 502, and the tool holder 410 is moved to a position in which the orifice is pressed against or is in close proximity to the patient's skin. The drive fluid is then introduced under pressure into the right side of the first chamber 496 through fluid port 500 to drive the first and second pistons 497 and 499 to the left in FIG. 37. As the second piston 499 moves to the left, it discharges the fluid through the orifice 502 and through the patient's skin into his body.

The tool holder 410 of the present invention can have an extremely compact design, so it can support and manipulate a medical tool inside tight spaces in which it would be difficult or impossible for a human operator to position a tool or in environments which would be unsafe for a human operator. In particular, the manipulator can hold a medical tool with respect to a patient inside medical imaging equipment, such as CT (computer tomography) equipment, conventional x-ray equipment, or magnetic resonance imaging equipment, which equipment often has a very small clearance surrounding a patient's body during imaging. Therefore, the tool holder enables the position of a medical tool with respect to a patient to be adjusted while imaging is taking place and makes it unnecessary to remove the patient from the imaging equipment each time the position of the tool needs to be adjusted. For this reason, the medical tool can be positioned quickly and accurately, enabling a medical procedure to be performed with the tool efficiently and economically with less stress on the patient. The ability of the tool to be rapidly positioned is particularly advantageous when the tool is being positioned in or near the patient's chest and the patient is holding his breath.

As will be appreciated, the tool holder 410 can be configured to hold a wide variety of medical tools both for therapeutic and diagnostic purposes, a few examples of which are biopsy needles, biopsy guns, catheters, various probes including cryo probes and radio frequency probes, lasers, laser hyperthermia devices, cameras, and needles for administering various substances, such as biotherapeutic agents, alcohol, or radioactive pellets, to the interior of a patient's body. In addition to tools which are inserted into a patient's body, the tool holder can be used to hold tools which are normally utilized on a patient's exterior. Moreover, the tool holder can be operated in a master-slave mode, a fully robotic mode, or a semi-robotic mode in which some of the motions of the tool holder are controlled by input commands from an operator and other motions are controlled automatically.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A manipulator for producing a remote center of revolute motion comprising:
    a base,
    a first parallelogram linkage mechanism including a first link pivotally mounted to the base for rotation about a first axis such that the first link moves in a first plane,
    a second parallelogram linkage mechanism including a second link pivotally mounted to the base for rotation about a second axis such that the second link moves in a second plane parallel to the first plane,
    the first link being pivotal about a third axis perpendicular to the first axis and the second link being pivotal about a fourth axis perpendicular to the second axis,
    the first and second parallelogram linkages being pivotally connected together by a first connector link and a second connector link, the first and second connector links being parallel to each other and parallel to the first and second axes such that the first and second planes remain parallel as the first and second links respectively rotate about the third and fourth axes,
    a tool holder pivotally connected to the first connector link by a first pivot joint and pivotally connected to the second connector link by a second pivot joint such that a tool held thereby is pivotable at a remote virtual pivot point about a first remote pivot axis by pivoting the first and second links respectively about the first and second axes and a second remote pivot axis by pivoting the first and second links respectively about the third and fourth axes.

2. The manipulator according to claim 1 wherein the remote virtual pivot point is offset from a line defined by the first and second pivot joints.

3. The manipulator according to claim 1 wherein the remote virtual pivot point is offset from a plane containing the third and fourth axes.

4. The manipulator according to claim 2 wherein the second connector link is attached to the first link at a point which is not co-linear with a line defined by the point at which the first link is attached to the base and a point at which the first connector link is connected to the first link and the second connector link is attached to the second link at a point which is not co-linear with a line defined by the point at which the second link is attached to the base and a point at which the first connector link is connected to the second link.

5. The manipulator according to claim 3 wherein the first pivot joint is offset from a line defined by the connections of the first connector link to the first and second links and the second pivot joint is offset from a line defined by the connections of the second connector link to the first and second links.

6. The manipulator according to claim 1 wherein the first parallelogram linkage mechanism is a four-bar linkage.

7. The manipulator according to claim 6 wherein the second parallelogram linkage mechanism is a four-bar linkage.

8. The manipulator according to claim 7 wherein the first parallelogram linkage mechanism and the second parallelogram linkage mechanism are separate four-bar linkages.

9. The manipulator according to claim 7 wherein the first parallelogram linkage mechanism and the second parallelogram linkage mechanism share a third link that extends parallel to the first and second links and is pivotally mounted to the base and share a fourth link that interconnects the first, second and third links and extends parallel to the base.

10. The manipulator according to claim 1 wherein at least one of the first and second parallelogram linkage mechanisms comprises a parallel gear linkage mechanism.

11. The manipulator according to claim 1 wherein at least one of the first and second parallelogram linkage mechanisms comprises a parallel chain linkage mechanism.

12. The manipulator according to claim 1 wherein at least one of the first and second parallelogram linkage mechanisms comprises a parallel mechanical belt linkage mechanism.

13. The manipulator according to claim 1 wherein the tool holder can move a tool held thereby linearly in a direction parallel to the line connecting the first and second pivot joints.

14. The manipulator according to claim 1 wherein the tool holder can move a tool thereby linearly in the direction corresponding to the line connecting the first and second pivot joints.

15. The manipulator according to claim 1 wherein the tool holder can rotate a tool thereby around a longitudinal axis of the tool.

16. The manipulator according to claim 1 wherein the tool holder is configured to hold a medical tool.

17. The manipulator according to claim 1 wherein the tool holder is adapted to sense forces applied to a tool held therein.

18. The manipulator according to claim 17 wherein the forces sensed by the tool holder are displayed for an operator.

19. The manipulator according to claim 17 wherein the forces sensed by the tool holder are reproduced as a force feedback for the operator in a haptic interface device.

20. The manipulator according to claim 1 wherein the manipulator is adapted to lock the tool holder in a desired position.

21. The manipulator according to claim 1 further including an actuator for driving movement of the first and second parallelogram mechanisms.

22. The manipulator according to claim 1 wherein the first and second parallelogram mechanisms are adapted to be moved manually by an operator.

23. The manipulator according to claim 1 wherein the first and second connector links included extended portions which extend beyond the first and second links.

24. The manipulator according to claim 1 wherein the extended portions of the first connector links extends in a direction parallel to the direction in which the extended portion of the second connector link extends.

25. The manipulator according to claim 24 wherein the extended portions of the first and second connector links extend in respective directions that are parallel to the base.

26. The manipulator according to claim 23 wherein the tool holder is pivotally connected to the extended portions of the first and second connector links.

27. The manipulator according to claim 1 wherein the tool holder includes a cartridge including a carriage for engaging a tool and a guide on which the carriage is movably mounted for translation along a path and a drive unit on which the cartridge is detachably mounted and which includes a drive mechanism drivably engageable with the carriage to move the carriage along the path.

28. The manipulator according to claim 27 further including a support which supports the drive unit for rotation about an axis transverse to the path of the carriage.

29. The manipulator according to claim 28 further including a drive mechanism coupled to the drive unit to rotate the drive unit about the axis.

30. The manipulator according to claim 27 wherein the cartridge includes a dispenser for dispensing a fluid.

31. A manipulator for producing a remote center of motion comprising:

a base, a parallelogram linkage mechanism including a first link pivotally connected to the base at a first pivot point for rotation about a first axis and a second link which extends parallel to the first link and is pivotally connected to the base at a second pivot point for rotation about a second axis, a third link pivotally connected to the second link and a fourth link which extends parallel to the third link and is pivotally connected to the second link, and a tool holder link pivotally connected at a third pivot point to the third link and pivotally connected to the fourth link at a fourth pivot point such that a tool held thereby is pivotable at a remote virtual pivot point about a first remote pivot axis wherein the remote pivot point is not both coplanar with the first and second axes and co-linear with a line defined by the first and second pivot points.

32. The manipulator according to claim 31 wherein the remote virtual pivot point is offset from a line defined by the first and second pivot points.

33. The manipulator according to claim 31 wherein the remote virtual pivot point is offset from a plane containing the first and second axes.

34. The manipulator according to claim 31 wherein the fourth link is attached to the second link at a fifth pivot point which is not co-linear with a line defined by the second pivot point and a sixth pivot point at which the third link is connected to the first link.

35. The manipulator according to claim 31 wherein the first and second links are pivotally connected to a fifth link which extends parallel to a line defined by the first and second pivot points at respective fifth and sixth pivot points and wherein the third pivot point is offset from a line defined by the fifth and sixth pivot points.

36. The manipulator according to claim 31 wherein the tool holder link can move a tool held thereby linearly in a direction parallel to the line connecting the third and fourth pivot joints.

37. The manipulator according to claim 31 wherein the tool holder link can move a tool held thereby linearly in the direction corresponding to the line connecting the third and fourth pivot joints.

38. The manipulator according to claim 31 wherein the tool holder link can rotate a tool held thereby around a longitudinal axis of the tool.

* * * * *